United States Patent [19]
Roos et al.

[11] Patent Number: 5,654,404
[45] Date of Patent: Aug. 5, 1997

[54] PROTECTION AGAINST LIVER DAMAGE BY HGF

[75] Inventors: Filip Roos, Brisbane; Ralph Schwall, Pacifica, both of Calif.

[73] Assignee: Genentech, Inc., So. San Francisco, Calif.

[21] Appl. No.: 419,654

[22] Filed: Apr. 10, 1995

Related U.S. Application Data

[62] Division of Ser. No. 310,361, Sep. 21, 1994, which is a continuation of Ser. No. 968,711, Oct. 30, 1992, abandoned, which is a continuation-in-part of Ser. No. 946,263, Sep. 16, 1992, abandoned.

[51] Int. Cl.$^6$ .................. C07K 14/435; C12P 21/08; A61K 39/00; A61K 38/16
[52] U.S. Cl. .................. 530/387.3; 530/350; 424/134.1; 424/136.1; 424/178.1
[58] Field of Search .............. 530/389.2, 387.3, 530/399, 350; 424/138.1, 124.1, 145.1; 514/12, 2

[56] References Cited

U.S. PATENT DOCUMENTS

| | | | |
|---|---|---|---|
| 5,004,805 | 4/1991 | Gohda et al. | 530/399 |
| 5,116,964 | 5/1992 | Capon et al. | 536/27 |
| 5,196,192 | 3/1993 | DeKretzer et al. | 424/85.8 |
| 5,227,158 | 7/1993 | Jardeau | 424/85.5 |
| 5,316,921 | 5/1994 | Godowski | 435/69.4 |

FOREIGN PATENT DOCUMENTS

| | | |
|---|---|---|
| 0456 188 A1 | 5/1990 | European Pat. Off. |
| 6172207 | 6/1974 | Japan |
| 62-45530 | 2/1987 | Japan |
| 2 288 899 | 11/1990 | Japan |
| 3 204 899 | 9/1991 | Japan |
| 4 030 000 | 1/1992 | Japan |
| 6025010 | 2/1994 | Japan |
| 6040938 | 2/1994 | Japan |
| 6145065 | 5/1994 | Japan |
| WO92/22321 | 12/1992 | WIPO |
| WO93/08821 | 5/1993 | WIPO |
| WO94/06909 | 3/1994 | WIPO |
| WO94/04175 | 3/1994 | WIPO |

OTHER PUBLICATIONS

An, W., et al., "Protective Effect of Hepatic Stimulator Substance Against Experimental Acute Liver Failure in Mice", *Acta Physiol Sin.*, 43(5):415–427 (1991).

An, W. et al., "A Study of the Protective Mechanism of Hepatic Stimulator Substance Against Experimental Acute Liver Failure In Mice" *Acta Physiol. Sin.*, 44(1):54–61 (1992)(Abstract Only).

Andus, et al., "Effects of Cytokines on the Liver", *Hepatology*, 13(2):364–375 (1991).Armendariz-Borunda, et al., "Regulation of TGFβ Gene Expression in Rat Liver Intoxicated with Carbon Tetrachloride", *FASEB J.*, 4:215–221 (1990).

Asami, et al., "Purification and Characterization of Hepatocyte Growth Factor from Injured Liver of Carbon Tetrachloride-Treated Rats", *J. Biochem.*, 109:8–13 (1991).

Awwad, et al., "Late Tissue Reactions After Single-Fraction Sequential Half-Body Irradiation (HBI) In Patients with Non-Hodgkin's Lymphomas", *Int. J. Radiat. Oncol. Biol. Phys.*, 19(5):1229–1232 (1990).

Baglin, et al., "Veno-Occlusive Disease of the Liver Complication ABMT Successfully Treated with Recombinant Tissue Plasminogen Activator (rt-PA)", *Bone Marrow Transplant*, 5(6):439–441 (1990).

Benhamou, J-Pierre, "Drug-Induced Hepatitis: Clinical Aspects", *Livers Cells and Drugs*, Chapter 164, pp.3–12, Colloque INSERM/John Libbey Eurotext Ltd., edited by A. Guillozo (1988).

Berse, et al., "Vascular Permeability Factor (Vascular Endothelial Growth Factor) Gene is Expressed Differentially in Normal Tissues, Macrophages, and Tumors", *Mol. Biol. Cell*, 3(2):211–220 (Feb. 1992).

Borisuth, et al., "Identification and Partial Characterization of TGF-β1 Receptors on Trabecular Cells", *Invest. Opthal. and Vis. Sci.*, 33:596–603 (Mar. 1992).

Bottaro, et al., "Identification of the Hepatocyte Growth Factor Receptor as the C-Met Proto-Oncogene Product", *Science*, 251:802–804 (1991).

Braun, et al., "Transforming Growth Factor β mRNA Increases During Liver Regeneration: A Possible Paracrine Mechanism of Growth Regulation", *Proc. Natl. Acad. Sci.*, 85:1539–1543 (Mar. 1988).

Carr, et al., "Inhibition of DNA Synthesis in Rat Hepatocytes by Platelet-Derived Type β Transforming Growth Factor", *Cancer Research*, 46:2330–2334 (1986).

Castilia, et al., "Transforming Growth Factors β, and α in Chronic Liver Disease", *New Engl. J. Med.*, 324:933-940 (Apr., 1991).

Chan, et al., "Identification of a Competitive HFG Antagonist Encoded by an Alternative Transcript", *Science*, 254:1382-1385 (1991).

Chelfetz, et al., "Isoform-Specific TGFβ Binding Proteins Sensitive to PIPLC", *J. Cell Biochem.*, 16(Part B):121 (Jan., 1992) (Abstract Only).

Cohen, et al., *Am. J. Surg.*, 145:529–533 (1983).

Cooper, "The Met Oncogene: From Detection by Transfection to Transmembrane Receptor for Hepatocyte Growth Factor", *Oncogene*, 7:3–7 (1992).

Cooper, et al., "Amplification and Overexpression of the Met Genen in Spontaneously Transformed NIH3T3 Mouse Fibroblasts", *EMBO J.*, 5:2623 (1986).

Cornelius, "Liver Function Tests in the Differential Diagnosis of Hepatotoxicity", *Hepatotoxicology*, Chapter 5, pp.181-185 (1991).

DePaolo, et al, "Follistatin and Activin: A Potential Intrinsic Regulatory System within Diverse Tissues" (43286A), Dept. of Molec. Endocrinol., La Jolla, CA:The Whittier Inst. for Diabetes and Endocrinol., pp.500–512 (1991).

Dong, et al., "Research on the Treatment of Severe Hepatitis and on the Mechanism of its Therapeutic Effectiveness", *Chinese J. of Internal Med.*, 30(10):637–639 (1991).

Dong, et al., "Study on Hepatocyte Growth Factor in the Treatment of Chronic Active Hepatitis", *J. China Med. Univ.*, 21(2):132–134 (1992) (Abstract Only).

Dong, et al., "Hepatocyte Growth Factor in the Treatment of Fulminant Viral Hepatitis and Its Therapeutic Mechanism", *J. China Med. Univ.*, 21(2):135–138 (1992).

Fajardo, et al., "Pathogenesis of Veno-occlusive Liver Disease After Radiation", *Arch. Pathol. Lab. Med.*, 104(11):584-8 (Nov. 1980).

Giordano, et al., "Tyrosine Kinase Receptor Indistinguishable from the C-Met Protein", *Nature*, 339:155 (May 1989).

Gohda, et al., "Purification and Partial Characterization of Hepatocyte Growth Factor from Plasma of a Patient with Fulminant Hepatic Failure", *J. Clin. Invest.*, 81:414–419 (Feb. 1988).

Gilman, et al., "Analgesic-Antipyretics and Antiinflammatory Agents", Goodman and Gilman's, *The Pharmacological Basis of Therapeutics*, 8th Edition, Gilman, et al., pp. 658–659 (1985).

Han, et al., "Characterization of the DNF15S2 Locus on Human Chromosome 3: Identification of a Gene Coding for Four Kringle Domains with Homology to Hepatocyte Growth Factor", *Biochem.*, 30:9768–9780 (1991).

Houck, et al., "Norepinephrine Modulates the Growth-Inhibitory Effect of Transforming Growth Factor-Beta in Primary Rat Hepatocyte Cultures", *J. Cell. Phys.*, 135:551–555 (1988).

Huang, et al., "Changes of Tumor Necrosis Factor Activity and Protective Effect of Hepatocyte Growth Factor and Prostaglandin E1 in Liver", *Zhonogguo Yike Daxue Xuebao*, 22:275-8 (1993) (Abstract Only).

Igawa, et al., "Hepatocyte Growth Factor is a Potent Mitogen for Cultured Rabbit Renal-Tubular Epithelial Cells", *Biochem. Biophys. Res. Commun.*, 174:831–838 (1991).

Lin, et al., "Expression Cloning of TGF-β Type II Receptor, a Functional Transmembrane Serine/Threonine Kinase, *Cell*, 68:775–785 (Feb., 1992).

Lin, et al., "Expression Cloning of the Type II TGF-β Receptor", *J. Cell. Biochem.*, 16 Part B:125 (Feb., 1992) (Abstract Only).

Lindroos, et al., "Hepatocyte Growth Factor (Hepatopoletin A) Rapidly Increases in Plasma before DNA Synthesis and Liver Regeneration Stimulated by Partial Hepatectomy and Carbon Tetrachloride Administration", *Hepatol.*, 13:734–750 (1991).

Ling, et al., "Pituitary FSH is released by a Heterodimer of the β-Subunits from the Two Forms of Inhibin", *Nature*, 321:779–782 (Jun., 1986).

Mason, et al., "Activin B: Precursor Sequences Genomic Structure and in Vitro Activities", *Molecular Endocrinology*, 3(9):1352–1358 (1989).

Mason, et al., "Human Inhibin and Activin: Structure and Recombinant Expression in Mammalian Cells", *Inhibin-Non-Steroidal Regulation of Follicle Stimulating Hormone Secretion*, Raven Press:Serono Symposia Publications, Vol. 42:77–88 (1987).

Mason, et al., "Structure of Two Human Ovarian Inhibin", *Biochem. and Biophys. Res. Comm.*, 135(3):957–964 (Mar., 1986).

Matsumoto, et al., "Hepatocyte Growth Factor is a Potent Simulator of Human Melanocyte DNA Synthesis and Growth", *Biochem. Biophys. Rec. Commun.*, 176:45–51 (1991).

Mbidde, et al., *Br. J. Cancer*, 58:779–782 (1988).

McCracken, et al., "Adjuvant Intrahepatic Chemotherapy with Mitomycin and 5-FU Combined with Hepatic Irradiation in High-Risk Patients with Carcinoma of the Colon: A Southwest Oncology Group Phase II Pilot Study", *Cancer Treat Rep.*, 69(1):129–31 (1985).

McIntyre, et al., "Fata Veno-Occlusive Disease of the Liver Following High-Dose 1,3-Bis (2-Chloroethyl)-1-nitrosourea (BCNU) and Autologous Bone Marrow Transplantation", *American Society of Clinical Pathologies*, 75(4):614–617 (1981).

Michalopoulos, *FASEB J.*, 4:176–1897 (1990).

Miyazawa, et al., "An Alternatively Processed mRNA Generated from Human Hepatocyte Growth Factor Gene", *Eur. J. Biochem.*, 197:15–22 (1991).

Miyazawa, et al., "Molecular Cloning and Sequence Analysis of cDNA for Human Hepatocyte Growth Factor", *Biochem. Biophys. Res. Comm.*, 163:967–973 (1989).

Montesano, et al., "Identification of a Fibroblast-Derived Epithelial Morphogen as Hepatocyte Growth Factor", *Cell*, 67:901–908 (1991).

Mordenti, et al., "The Use of Interspecies Scaling in Toxicokinetics", *In Toxicokinetics and New Drug Development*, Yacobi, Skelly and Batra, Eds., Pergamon Press, New York, pp. 42–96 (1989).

Moriyama, et al., "Immunobiology and Pathogenesis of Hepatocellular Injury in Hepatitis B Virus Transgenic Mice", *Science*, 248:361–364 (1990).

Moulder, et al., "Hepatic Function and Drug Pharmacokinetics After Total Body Irradiation Plus Bone Marrow Transplant", *Int. J. Radiat. Oncol Biol. Phys.*, 19:1389–1396 (1990).

Nakamura, et al., "Inhibitory Effect of Transforming Growth Factor-β on DNA Synthesis of Adult Rat Hepatocytes in Primary Culture", *Biochem. & Biophys. Res. Comm.*, 133(3):1042–1050 (1985).

Nakamura, et al., "Interleukin-1β is a Potent Growth Inhibitor of Adult Rat Hepatocytes in Primary Culture", *Exp. Cell Research*, 179:488–497 (1988).

Nakamura, et al., "Isolation and Characterization of Native Activin B", *The J. of Biol. Chem.*, 267(23):16385–16389 (Aug., 1992).

Nakamura, et al. "Purification and Subunit Structure of Hepatocyte Growth Factor from Rat Platelets", *FEBS Letters*, 224:311–316 (1987).

Nakamura, et al., "Partial Purification and Characterization of Hepatocyte Growth Factor from Serum of Hepatectomized Rats", *Biochem. Biophys. Res. Comm.*, 122:1450–1459 (1984).

Nakamura, et al., "Purification and Characterization of a Growth Factor from Rat Platelets for Mature Parenchymal Hepatocytes in Primary Cultures", *Proc. Natl. Acad. Sci. USA*, 83:6489–6493 (1986).

Nakamura, et al., "Molecular Cloning and Expression of Human Hepatocyte Growth Factor", *Nature*, 342:440–443 (1989).

Naldini, et al., "Scatter Factor and Hepatocyte Growth Factor are Indistinguishable Ligands for the MET Receptor", *EMBO J.*, 10:2867–2878 (1991).

Naldini, et al., "Hepatocyte Growth Factor (HGF) Stimulates the Tyrosine Kinase Activity of the Receptor Encoded by the Proto-Oncogene c-MET", *Oncogene*, 6:501–504 (1991).

Oberhammer, et al., "Effect of Transforming Growth Factor β on Cell Death of Cultured Rat Hepatocytes", *Cancer Research*, 51:2478–2485 (1991).

Okajima, et al., "Primary Structure of Rat Hepatocyte Growth Factor and Induction of Its mRNA During Liver Regeneration Following Hepatic Injury:, *Eur. J. Biochem.*, 193:375–381 (1990).

Park, et al., "Sequence of MET Protooncogene cDNA has Features Characteristic of the Tyrosine Kinase Family of Growth-Factor Receptors", *Proc. Natl. Acad. Sci. USA*, 84:6379–6383 (1987) Pergamon Press, 658–659 (1990).

Rivier, et al., "Effect of Recombinant Activin-A on Gonadotropin Secretion in the Female Rat", *Endocrinology*, 129(5):2463–2465 (1991).

Rosen, et al., "Scatter Factor and Its Relationship to Hepatocyte Growth Factor and Met", *Cell Growth and Differentiation*, 2:603 (1991).

Rosti, et al. "Alteplase for Hepatic Veno-Occlusive Disease After Bone Marrow Transplantation", *Lancet*, 339:1481–1482 (1992).

Rubin, et al., "A Broad-Spectrum Human Lung Fibrobalst-Derived Mitogen is a Variant of Hepatocyte Growth Factor", *Proc. Natl. Acad. Sci. USA*, 86:415–419 (1991).

Russell, et al., "Type β Transforming Growth Factor Reversibly Inhibits the Early Proliferative Response to Partial Hepatectomy in the Rat", *Proc. Natl. Acad. Sci.*, 85:5128–5130 (1988).

Schwall, et al., "Multiple Actions of Recombinant Activin-A In Vivo", *Endocrinology*, 125(3):1420–1423 (1989).

Schwall, et al., "Recombinant Expression and Characterization of Human Activin A", *Molec. Endocrinology*, 2(12);1237–1242 (1988).

Schwall, et al., *Hepatol.*, 18:347–356 (1993).

Schwall, et al., *FASEB J.*, J7(3–4):A28 (1993).

Segarini, et al., "Two Novel Patterns of Transforming Growth Factor β (TGF-β) Binding to Cell Surface Proteins are Dependent upon the Binding of TFG-β1 and Indicate a Mechanism of Positive Cooperativity", *J. Biol. Chem.*, 267:1048–1053 (Jan., 1992).

Seki, et al., "Isolation and Expression of cDNA for Different Forms of Hepatocyte Growth Factor from Human Leukocyte", *Biochem. and Biophys. Res. Commun.*, 172:321–327 (1990).

Sinclair, et al., "Drug-Induced Hepatic Injury", *Textbook of Internal Medicine*, 569–575 (1992).

Stoker, et al., "Scatter Factor is a Fibrobalst-Derived Modulator of Epithelial Cell Mobility", *Nature*, 327:239–242 (1987).

Strain, et al., "Transforming Growth Factor β Inhibits DNA Synthesis in Hepatocytes Isolated from Normal and Regenerating Rat Liver", *Biochem. and Biophys. Res. Comm.*, 145(1):436–442 (1987).

Strain, et al., "Native and Recombinant Human Hepatocyte Growth Factors are Highly Potent Promoters of DNA Synthesis in both Human and Rat Hepatocytes", *J. Clin. Invest.*, 87:1853–1857 (1991).

Tajima, et al., *FEBS Lett.*, 291(2):229–232 (1991).

Tashiro, et al, "Deduced Primary Structure of Rat Hepatocyte Growth Factor and Expression of the mRNA in Rat Tissues", *Proc. Natl. Acad. Sci. USA*, 87:3200–3204 (1990).

Theodorescu, et al. *J. Cell. Phys.*, 148:380–390 (1991).

Tsubouchi, et al., "Prediction of Outcome in Fulminant Hepatic Failure by Serum Human Hepatocyte Growth Factor", *The Lancet*, 340:307 (Aug. 1992).

Vale, et al., "Chemical and Biological Characterization of the Inhibin Family of Protein Hormones", *Recent Progress in Hormone Research*, 44:1–34 (1988).

Vale, et al., "Purification and Characterization of an FSH Releasing Protein from Porcine Ovarian Follicular Fluid", *Nature*, 321:776–779 (Jun., 1986).

Wang, et al., "Expression Cloning of the Type III TGF-β Receptor", *J. Cell. Biochem.*, 16 Part B:129 (Feb., 1992) (Abstract Only).

Wang, CB, "Treatment of Severe Chronic Hepatitis B by Combination of Traditional Chinese Medicine and Western Medicine and Western Medicine Therapy—With An Analysis of 122 Cases", *Chung Hua Nei Ko Tsa Chih*, (China) 12(4):203–6, 195 (Apr., 1992).

Weidner, et al., "Scatter Factor: Molecular Characteristics and Effect on the Invasiveness of Epithelial Cells", *J. Cell. Biol.*, 111:2097–2108 (1990).

Yasuda, et al., *Gastroenterology*, 140(4):A1022.

Ying, Shao-Yao, "Inhibins, Activins, and Foilistatins: Gonadal Proteins Modulating the Secretion of Follicle-Stimulating Hormone", *Endocrine Reviews*, 9(2):267–293 (1988).

Zarnegar, et al., "$NH_2$-Terminal Amino Acid Sequence of Rabbit Hepatopoietin A, A Heparin-Binding Ploypeptide Growth Factor for Hepatocytes", *Biochem, Biophys. Res. Comm.*, 163:1370–1376 (1989).

Zarnegar, et al., "Purification and Biological Characterization of Human Hepatopoietin A, A Polypeptide Growth Factor for Hepatocytes", *Cancer Research*, 49:3314–3320 (1989).

Zazhi, *Chinese J. of Internal Med.*, 30(10):637–639 (1991).

Zheng, et al., "Investigation on Protective Effect of Hepatocyte Growth Factor From Carbon Tetrachloride-Induced Chronic Toxic Liver injury", *Tianjin Med. J.*, 18(9):539–541 (1990) (Abstract Only).

Zhou, et al., "Hepatocyte Stimulatory Peptide and its Clinical Significance in Viral Hepatitis", *Chung Hua Nei Ko Tsa Chih*, (China) 31(10):626–8, (Oct., 1992) (Abstract Only).

*Primary Examiner*—Lila Feisee
*Assistant Examiner*—John Lucas
*Attorney, Agent, or Firm*—Merchant, Gould, Smith, Edell, Welter & Schmidt

[57]  ABSTRACT

The present invention provides methods for preventing occurrence or progression of liver damage using hepatocyte growth factor. In the methods, a preventatively effective amount of the hepatocyte growth factor is administered to the patient. The hepatocyte growth factor can be administered, for instance, prior to administering a hepatotoxic therapy to the patient. The hepatocyte growth factor can further be administered with activin or transforming growth factor-beta to prevent liver damage. Compositions comprising hepatocyte growth factor and activin antagonist or transforming growth factor-beta antagonist are also provided by the invention.

18 Claims, 5 Drawing Sheets

PROTECTION AGAINST LIVER DAMAGE BY HGF

This application is a divisional of application Ser. No. 08/310,361 filed on 21 Sep. 1994, which is a continuation application of Ser. No. 07/968,711 filed on 30 Oct. 1992, now abandoned, which is a continuation-in-part application of Ser. No. 07/946,263 filed on 16 Sep. 1992, now abandoned, which applications are incorporated herein by reference.

FIELD OF THE INVENTION

The present invention concerns the use of hepatocyte growth factor (HGF) for the prevention of liver damage.

BACKGROUND ART

Liver damage occurs in a number of acute and chronic clinical conditions, including drug-induced hepatotoxicity, viral infections, vascular injury, autoimmune disease and blunt trauma. In addition, patients subject to inborn errors of metabolism may be at risk for developing liver damage. Symptoms of liver damage occurring as a result of these clinical conditions include, for example, fulminant hepatic failure with cholestasis, hepatic lesions, and liver tissue necrosis, and in many instances, the restoration of normal liver function is vital to the survival of patients.

Hepatotoxic compounds can induce almost all types liver injury (Benhamou, J-Pierre, *Liver Cells and Drugs*, Chapter 164, pgs. 3–12, Colloque INSERM/John Libbey Eurotext Ltd., edited by A. Guillozo (1988). The susceptibility of the liver to damage by chemical agents may be related to its primary role in drug metabolism or is a consequence of hypersensitivity reactions. Up to 25% of cases of fulminant hepatic failure may be the result of adverse reactions to medical agents. Hepatotoxic compounds are also an important cause of chronic liver disease including fatty liver, hepatitis, cirrhosis and vascular and neoplastic lesions of the liver. (Sinclair et al., *Textbook of Internal Medicine*, 569–575 (1992) (editor, Kelley; Publisher, J. B. Lippincott Co.).

Hepatotoxic compounds may induce liver damage by cytotoxicity to the liver directly or through the production of toxic metabolites (this category includes the hypersensitivity reaction which mimics a drug allergy); cholestasis, an arrest in the flow of bile due to obstruction of the bile ducts; and vascular lesions, such as in veno occlusive disease (VOD), where injury to the vascular endothelium results in hepatic vein thrombosis. Individual susceptibility to liver damage induced by hepatotoxic compounds is influenced by genetic factors, age, sex, nutritional status, exposure to other drugs, and systemic diseases (Sinclair et al., *Textbook of Internal Medicine*, Supra). Hepatotoxic compounds known to induce liver damage include acetaminophen, nitrosoureas, used in the treatment of cancer, and isoniazid, used in the treatment of tuberculosis.

Although in minor liver damage induced by hepatotoxic compounds, withdrawal of the causative agent may be sufficient to substantially reverse the damage occurred, in many instances where fulminant hepatic failure ensues, aggressive medical therapy, including the administration of antidotes, such as N-acetylcysteine, may be required. A antidotal treatment is, however, often not effective when given more than about 10–24 hours after exposure to the hepatotoxic compound (Goodman and Gilman's. *The Pharmacological Basis of Therapeutics* 8th edition, Gilman et al., Pergamon Press, 658–659 (1990)). If this happens, the liver damage may become permanent and life threatening, leaving liver transplantation as the only remedy.

Radiation therapy can also induce liver damage. It has been shown that hypoalbuminemia and decreased hepatic blood flow, both symptoms of liver damage, occur after single-dose total body irradiation (Moulder, J. et al. *Int J Radiat Oncol Biol Phys* 19: 1389–1396 (1990)). Awwad, H. et al., *Int J Radiat Oncol Biol Phys* 19(5): 1229–1232 (1990) show that lung and hepatic toxicities constitute the main radiation-related damage after half-body irradiation used as the treatment for patients with non-Hodgkin's lymphomas and recommend low dose-rate or multifraction irradiation in order to reduce the risk of liver toxicity. McCracken, J. et al., *Cancer Treat Rep* 69(1): 129–31 (1985) caution that combined radiotherapy and intra-arterial chemotherapy may result in significant chronic liver damage, as monitored by serum enzyme levels, and recommend exercising caution in the future use of the therapy. Fajardo, L. et al. *Arch Pathol Lab Med* 104(11): 584–8 (1980) show that radiation-induced liver disease is characterized structurally by progressive fibrous obliteration of central veins (VOD) and that in several patients, VOD occurred at radiation doses conventionally considered safe.

Inborn errors of metabolism exist which result in liver damage. Patients who have a genetically limited capacity to convert aryl epoxides to nontoxic dihydriols, seem predisposed to developing liver damage from exposure to phenytoin and halotane, drugs useful as anesthetics. Also, susceptibility to contraceptive steroid-associated cholestasis appears to have a strong genetic component (Sinclair et al., *Textbook of Internal Medicine*, Supra).

Liver damage of any origin can be diagnosed and monitored by biochemical tests of liver markers, such as assessment of hepatic blood flow or prothrombin clotting time, or serum markers, such as serum bilirubin, serum transaminase, and serum alkaline phosphatase levels and (Cornelius, C., *Hepatotoxicology* pg, 181, (1991) and (Awwad, H. *Int J Radiat Oncol Biol Phys* 19(5): 1229–1232 1990)). Liver damage can also be monitored from histological evaluation of liver tissue, which is helpful in determining the type and extent of liver damage (Sinclair, S. *Textbook of Internal Medicine*, Supra. It is known that results from in vitro biochemical tests measuring liver function or serum markers and/or results from liver tissue biopsy, correlate with in vivo liver damage assessment. Often, a combination of biochemical tests, tissue biopsy, patient medical history, and assessment of means inducing liver damage is used in determining the extent of liver damage.

Liver cell (hepatocyte) regeneration is believed to be controlled by various growth stimulatory and growth inhibitory cytokines of autocrine or paracrine origin, however, the exact role and action mechanism of these factors is far from entirely understood.

In vitro, DNA synthesis in isolated hepatocytes has been shown to be stimulated by growth factors such as epidermal growth factor (EGF) and type a transforming growth factor (TGF-α) and to be inhibited by interleukin 1β (IL-1β) (Nakamura et al., *Exp. Cell Res.*, 179: 488–497 (1988)), transforming growth factor β1 (TGF-β1) (Braun et al., *Proc. Natl. Acad. Sci. USA*, 85: 1539–1543 (1988); Nakamura et al., *Biochem. Biophys. Res. Comm.*, 133: 1042–1050 (1985); Carr et al., *Cancer Res.*, 46: 2330–2334 (1986); Castilla et al., *New Eng. J. Med.*, 324: 933–940 (1992); Houck et al., *J. Cell. Physiol.*, 135: 551–555 [1988]; Strain et al., *Biochem. Biophys. Res. Commun.*, 145: 436–442 (1987)), and activin (U.S. patent Application Ser. No. 07/712,284 filed 10 Jun.

1991). TGF-β1 has been shown to inhibit in vivo DNA synthesis taking place after partial hepatectomy. Russell et al., *Proc. Natl. Acad. Sci. USA*, 85: 5126–5130 (1988). Vascular endothelial growth factor (VEGF), an endothelial cell mitogen, is expressed in the normal liver (Berse, et al., *Mol. Biol. Cell*, 3(2): 211–220 (1992)), where it plays a role in tissue nutrition and waste removal.

More recently, a further protein, named hepatocyte growth factor (HGF) has been shown to be a complete mitogen for primary hepatocytes. Although based upon the observation that the level of HGF in the serum rapidly increases following experimental damage to the liver and in patients with fulminate hepatic failure it has been proposed that HGF may be an important mediator of liver regeneration in vivo, and certain experimental evidence supports this hypothesis, there is no clear consensus among scientists about the role of HGH in liver regeneration. Rosen et al., *Cell Growth and Differentiation* 2: 603 (1991) caution that markedly elevated HGF levels in patients with chronic liver disease may indicate that HGF is a marker for or instigator of human liver damage rather than a repair factor.

Growth factors, proteins with growth factor-like activities, such as cytokines, (Andus et al., *Hepatology* 13(2): 364–375 (1991)) and therapeutics, such as tissue plasminogen activator (Baglin, et al., *Bone Marrow Transplant* 5(6): 439–441 (1990)), have been indicated in the treatment of liver damage.

HGF was purified by Nakamura et al. from the serum of partially hepatectomized rats (Biochem. Biophys. Res. Comm. 122: 1450–1459 (1984)). Subsequently, HGF was purified from rat platelets, and its subunit structure was determined (Nakamura et al., *Proc. Natl. Acad. Sci. USA*, 83, 6489–6493 (1986); and Nakamura et al., *FEBS Letters* 224, 311–316 (1987)). The purification of human HGF (hHGF) from human plasma was first described by Gohda et al., *J. Clin. Invest.* 81, 414–419 (1988). According to the results reported by Gohda et al. hHGF is more effective in the stimulation of cultured hepatocyte proliferation than human epidermal growth factor (hEGF) or insulin, and the effect of hHGF with the maximal effects of hEGF and insulin is "additive or synergistic". Similarly, Zarnegar et al., *Cancer Research* 49, 3314–3320 (1989) described the purification of a polypeptide growth factor, called human hepatopoietin A (HPTA) having very similar properties to hHGF as characterized in earlier publications. As the authors do not disclose the amino acid sequences of their purified proteins, the degree of the structural similarity between the two factors can not be determined.

The N-terminal amino acid sequence of rabbit HPTA was described by Zarnegar et al., *Biochem. Biophys. Res. Comm.* 163, 1370–1376 (1989).

Both rat HGF and hHGF have been molecularly cloned, including the cloning and sequencing of a naturally occurring variant lacking 5 amino acids in the Kringle 1 (K1) domain, designated "delta5 HGF" (Miyazawa et al., *Biochem. Biophys. Res. Comm.* 163: 967–973 (1989); Nakamura et al., *Nature* 342: 440–443 (1989); Seki et al., *Biochem. and Biophys. Res. Commun.* 172: 321–327 (1990); Tashiro et al., *Proc. Natl. Acad. Sci. USA* 87: 3200–3204 (1990); Okajima et al., *Eur. J. Biochem.* 193: 375–381 (1990)). The sequences reported by Miyazawa et al. and Nakamura et al. for hGH differ at several positions. The comparison of the amino acid sequence of rat HGF with that of hHGF revealed that the two sequences are highly conserved and have the same characteristic structural features. The length of the four Kringle domains in rat HGF is exactly the same as in huHGF. Furthermore, the cysteine residues are located in exactly the same positions; an indication of similar three-dimensional structures (Okajima et al., Supra; Tashiro et al., Supra).

A naturally occurring hHGF variant has recently been identified which corresponds to an alternative spliced form of the hHGF transcript containing the coding sequences for the N-terminal finger and first two kringle domains of mature hHGF (Chan et al., *Science* 254: 1382–1385 (1991); Miyazawa et al., *Eur. J. Biochem.* 197: 15–22 (1991)). This variant, designated HGF/NK2, has been proposed to be a competitive antagonist of mature hHGF.

The HGF receptor has been identified as the product of the c-Met proto-oncogene (Bottaro et al., *Science* 251: 802–804 (1991); Naldini et al., *Oncogene* 6: 501–504 (1991)), and 190-kDa heterodimeric (a disulfide-linked 50-kDa a-chain and a 145-kDa β-chain) membrane-spanning tyrosine kinase protein (Park et al., *Proc. Natl. Acad. Sci. USA* 84: 6379–6383 (1987)). The c-Met protein becomes phosphorylated on tyrosine residues of the 145-kDa β-subunit upon HGF binding.

The levels of HGF increase in the plasma of patients with hepatic failure (Gohda et al., Supra) and in the plasma (Lindroos et al., *Hepatol.* 13: 734–750 (1991)) or serum (Asami et al., *J. Biochem.* 109: 8–13 (1991)) of animals with experimentally induced liver damage. The kinetics of this response is rapid, and precedes the first round of DNA synthesis during liver regeneration suggesting that HGF may play a key role in initiating this process. Although HGH was originally thought to be a liver-specific mitogen, more recently, it has been shown to be a mitogen for a variety of cell types including melanocytes, renal tubular cells, keratinocytes, certain endothelial cells and cells of epithelial origin (Matsumoto et al., *Biochem. Biophys. Res. Commun.* 176: 45–51 (1991); Igawa et al., *Biochem. Biophys. Res. Commun.* 174, 831–838 (1991); Han et al., *Biochem.* 30: 9768–9780 (1991); Rubin et al., *Proc. Natl. Acad. Sci. USA* 88: 415–419 (1991)). Interestingly, HGF can also act as a "scatter factor", an activity that promotes the disassociation of epithelial and vascular endothelial cells in vitro (Stoker et al., *Nature* 327: 239–242 (1987); Weidner et al., *J. Cell Biol.* 111: 2097–2108 (1990); Naldini et al., *EMBO J.* 10: 2867–2878 (1991)). Moreover, HGF has recently been described as an epithelial morphogen (Montesano et al., *Cell* 67: 901–908 (1991)). Therefore, HGF has been postulated to be important in tumor invasion and in embryonic development. Chronic c-Met/HGF receptor activation has been observed in certain malignancies (Cooper et al., *EMBO J.* 5: 2623 (1986); Giordano et al., *Nature* 339: 155 (1989)).

Activin consists of a homodimer or heterodimer of inhibin β subunits, which may be $\beta_A$ or $\beta_B$ subunits. Vale et al., *Recent Prog. Horm. Res.*, 44: 1–34 (1988). There is 95–100% amino acid conservation of β subunits among human, porcine, bovine, and rat activins. The $\beta_A$ and $\beta_B$ subunits within a given species are about 64–70% homologous.

The activin $\beta_A$ and $\beta_B$ homodimers ("Activin A" and "Activin B," respectively) have been identified in follicular fluid, and both molecules have been cloned and their genes expressed. Mason et al., *Biochem. Biophys. Res. Commun.*, 135: 957 (1986); EP Pub. No. 222,491 published May 20, 1987; Mason et al., *Molecular Endocrinol.*, 3: 1352–1358 (1989); Schwall et al., *Mol. Endocrinol.*, 2: 1237–1242 (1988); Nakamura et al., *J. Biol. Chem.*, 267: 16385–16389 (1992). The complete sequence of the $\beta_B$ subunit is published in Serono Symposium Publications, entitled "Inhibin- Non-Steroidal Regulation of Follicle Stimulating Hormone Secretion", eds. H. G. Burger et al., abstract by A. J. Mason et al., vol. 42, pp. 77–88 (Raven Press, 1987), entitled "Human Inhibin and Activin: Structure and Recombinant Expression in Mammalian Cells." The recombinant molecule has been shown to increase serum levels of FSH in rats when delivered by subcutaneous injection. Schwall et al., *Endocrinol.*, 125: 1420–1423 (1989); Rivier and Vale, *Endocrinol.*, 129: 2463–2465 (1991).

Activin was initially identified in follicular fluid as a naturally occurring gonadal peptide involved in the regulation of the secretion of follicle-stimulating hormone (FSH) by rat anterior pituitary cells. Vale et al., *Nature*, 321: 776–779 (1986); Ling et al., *Nature*, 321: 779–782 (1986); DePaolo et al., *Proc. Soc. Exp. Biol. Med.*, 198: 500–512 (1991); Ying, *Endocrine Rev.*, 9: 267–293 (1988).

Subsequent studies of activin revealed other activities, including the effects on follicular granulosa cell differentiation (Sugino et al., *Biochem. Biophys. Res. Commun.*, 153: 281–288 [1988]), spermatogonial proliferation (Mather et al., *Endocrinol.*, 127: 3206–3214 [1990]), erythroid differentiation (EP Publ. No. 210,461 published Feb. 4, 1987; Eto et al., *Biochem. Biophys. Res. Commun.*, 142: 1095–1103 [1987]; Murata et al., *Proc. Natl. Acad. Sci. USA*, 85: 2434–2438 [1988]; Yu et al., *Nature*, 330: 765–767 [1987], stimulation of insulin secretion by pancreatic islets (Totsuka et al., *Biochem. Biophys. Res. Commun.*, 156: 335–339 [1988]), enhancement of proliferation of fibroblast (Hedger et al., *Mol. Cell Endocrinol.*, 61: 133–138 [1989]), stimulation of a dose-dependent increase in inositol phosphates in rat parenchymal liver cells, an effect also seen with EGF (Mine et al., *Biochem. Biophys. Res. Comm.*, 186: 205–210 [1992]), modulation of somatotroph functions (Billestrup et al., *Mol. Endocrinol.*, 4:356–362 [1990]), modulation of nerve cell differentiation (Schubert et al., *Nature*, 344: 868–870 [1990]; Hashimoto et al., *Biochem. Biophys. Res. Comm.*, 173: 193–200 [1990]), and mesoderm induction. Smith et al., *Nature*, 345: 729–731 (1990); Mitrani et al., *Cell*, 63: 495–501 (1990).

It has also been found that chronic renal failure serum contains as much activin as normal serum, but the difference between normal serum and the serum of patients with renal failure exists in the context of a specific inhibitor of activin, with the suggestion that activin could be utilized in the therapy of the anemia of such patients. Shiozaki et al., *Biochem. Biophys. Res. Commun.*, 183: 273–279 (1992). While these activities have been demonstrated in vitro, the role of activin in vivo remains poorly understood.

Inhibin and activin are members of a family of growth and differentiation factors. The prototype of this family is TGF-$\beta$ (Derynck et al., *Nature*, 316: 701–705 (1985)), which, according to one source, also possesses FSH-releasing activity (Ying et al., *Biochem. Biophys. Res. Commun.*, 135: 950–956 (1986). Other members of the TGF-$\beta$ family include the Mullerian inhibitory substance, the fly decapentaplegic gene complex, and the product of Xenopus Vg-1 mRNA.

TGF-$\beta$1 appears to be a negative regulator of liver growth, and the TGF-$\beta$ molecule is associated with regression of other epithelial tissues in the embryo (Silberstein and Daniel, *Science*, 237: 291–293 [1987]) or adult (Kyprianou and Isaacs, supra) and of certain cancers. Kyprianou et al., *Cancer Res.*, 51: 162–166 (1991). Recently, it was reported that cell proliferation and apoptosis are coordinately regulated by TGF-$\beta$1 in cultured uterine epithelial cells. Rotello et al., *Proc. Natl. Acad. Sci. USA*, 88: 3412–3415 (1991).

Apoptosis is a physiological cell death wherein the nucleus condenses and the cytoplasm fragments.

Studies in vivo showed that apoptotic hepatocytes in normal and prenoeplastic liver exhibited immunostaining for TGF-$\beta$1. Oberhammer et al., *Naunyn-Schmiedeberg's Arch. Pharmacol. Suppl.*, 343: R24 (1991). See also Oberhammer et al., *Cancer Res.*, 51: 2478–2485 (1991). Evidence has now been found that hepatocyte death induced by TGF-$\beta$1 in vitro is indeed apoptosis. Oberhammer et al., *Proc. Natl. Acad. Sci. USA*, 89: 5408–5412 (1992).

A new class of gonadal protein factors, named follistatin or FSH-suppressing protein (FSP), has been isolated from side fractions derived from purifying porcine and bovine ovarian inhibins and activins. Ying, *Endoc. Rev.*, 9: 267–293 (1988); Ling et al., "Isolation and characterization of gonadal polypeptides that regulate the secretion of follicle stimulating hormone," in Hodgen et al., eds., *Non-Steroidal Gonadal Factors: Physiological Roles and Possibilities in Contraceptive Development*, Jones Institute Press, Virginia, (1988), pp. 30–46. Follistatin was initially characterized by its ability to suppress FSH secretion from the pituitary. The action of follistatin is apparently similar to that of inhibin, but structurally the two proteins are quite different. Ueno et al., *Proc. Natl. Acad. Sci. USA*, 84: 8282–8286 (1987); Robertson et al., *Biochem. Biophys. Res. Commun.*, 149: 744–749 (1987).

Follistatin is a glycosylated single-chain protein that is found in forms having molecular weights ranging from 31 to 39 kDa. All of these forms have similar amino acid compositions and identical amino-terminal amino acid sequences. The molecular cloning of cDNA with the gene of follistatin revealed two forms, a smaller molecular weight form and a larger form, which are generated by alternative splicing. The smaller form represents a carboxy-terminal truncated form of the larger precursor.

Recent examinations of follistatin gene expression in rat tissues have shown that follistatin mRNA is detected not only in the gonads but also in the kidney, decidual tissue, pancreas, cerebral cortex, pituitary, etc. Shimasaki et al., *Mol. Endocrinol.*, 3: 651–659 (1989); Kaiser et al., *Endocrinology*, 126: 2768–2770 (1990); Michel et al., *Biochem. Biophys. Res. Comm.*, 173: 401–407 (1990).

It has been found that follistatin is able to neutralize the diverse actions of activin in various systems such as stimulation of FSH secretion by cultured pituitary cells (Kogawa et al., *Endocrinology*, 128: 1434–1440 [1991]) and induction of mesodermal tissue formation in Xenopus oocytes. Asashima et al., *Arch. Dev. Biol.*, 200: 4–7 (1991). It has been found, in fact, that immunoreactive follistatin is widespread in rat tissues, including hepatic cells, which demonstrated homogeneous immunoreactivity from moderate to strong. Kogawa et al., *Endocrinol. Japan*, 38: 383–391 (1991). The authors suggest that follistatin is a ubiquitous protein regulating a wide variety of activin actions.

There exists a need for an effective therapy for the prevention of liver damage. This need exists in any patient population in which chronic or acute liver damage has been induced, for example by hepatotoxic compounds, radiation exposure, viral infection, autoimmune disease, elevated in vivo levels of proteins, including liver cell growth inhibitory proteins, hepatotoxic proteins and cytokines, or genetic factors, and where it is desirable to inhibit the progression of such damage. This need further exists in a patient population at risk of developing liver damage, such as in the case of drug overdose, in the case of accidental exposure to infected blood samples, or in a clinical scenario which includes aggressive chemotherapy or radiation therapy.

In many instances, the treatment of serious, life threatening conditions, such as cancer, is severely limited by the hepatotoxicity of the chemotherapeutic agents and/or radiation therapy employed. It would be desirable to be able to expose patients to higher doses of such chemotherapeutics or radiation therapy for an extended period of time without the risk of severe liver damage. There is a related need for an effective liver damage preventative agent which could be included in a clinical protocol potentially inducing liver damage.

It would be particularly desirable to provide means for the prevention of the further progression of liver damage in situations where early intervention is critical. This would be particularly beneficial when known antidotes are no longer effective because of the time elapsed since the exposure to the causative factor of liver damage.

Accordingly, it is an object of the present invention to provide means for the prevention of liver damage in patients at risk of developing liver damage, especially due to hepatotoxic compounds, radiation, or genetic predisposition.

It is another object to provide means for the prevention of the progression of liver damage already occurred.

It is a further object to enable the extended exposure of patients to potentially hepatotoxic treatments and/or to increase the dose of such treatments by preventing the (further) development of liver damage.

It is a still further object of the present invention to provide means for early intervention in patients showing symptoms of a risk of developing liver damage.

It is another object to provide means for preventing the progression of liver damage at a time when antidotes known in the art would no longer be effective.

These and further objects will be apparent to one of ordinary skill in the art.

SUMMARY OF THE INVENTION

The present invention is based on the experimental finding that HGF provides effective protection from anticipated liver damage due to the administration of a hepatotoxic compound, and in particular, from anticipated liver tissue necrosis and anticipated elevated serum enzyme levels, both indicative of liver damage. The present invention is also based on the experimental finding that HGF provides protection from activin and TGF-β induced cell death in hepatocytes. We have further found that HGF is capable of preventing the progression of liver damage already occurred. Although HGF has been associated with hepatocyte regeneration, its ability to prevent the occurrence or further progression of liver damage is entirely unexpected.

In one aspect, the present invention relates to a method for the prevention of the establishment or progress of liver damage in a patient at risk of developing or having been diagnosed with liver damage comprising administering to the patient a preventatively effective amount of hepatocyte growth factor (HGF). The patient preferably is mammalian, more preferably human.

Potential or actual liver damage may be due to numerous external or internal factors, including intentional or accidental exposure to a hepatotoxic compound, radiation exposure, genetic predisposition, autoimmune disease and viral infections of the liver.

In another aspect, the invention concerns a composition comprising a therapeutically effective amount of a hepatotoxic therapeutic agent and a liver damage preventative amount of HGF.

In a further embodiment, the invention relates to a method for the treatment of a patient with a hepatotoxic therapeutic agent effective in the prevention or treatment of a disorder or pathologic physiological condition, comprising:

a) administering to said patient, simultaneously or in optional order, a biologically effective dose of said therapeutic agent and a preventatively effective amount of HGF, b) monitoring said patient for indication of liver damage, and c) continuing said treatment until said disorder or condition is eliminated or until liver damage is indicated.

In yet a further embodiment, the present invention relates to a method for the prevention of the establishment or progress of liver damage in a patient at risk for developing or having been diagnosed with viral or autoimmune hepatitis comprising administering to said patient a liver damage preventative amount of HGF.

DETAILED DESCRIPTION OF THE INVENTION

Figure 1A:
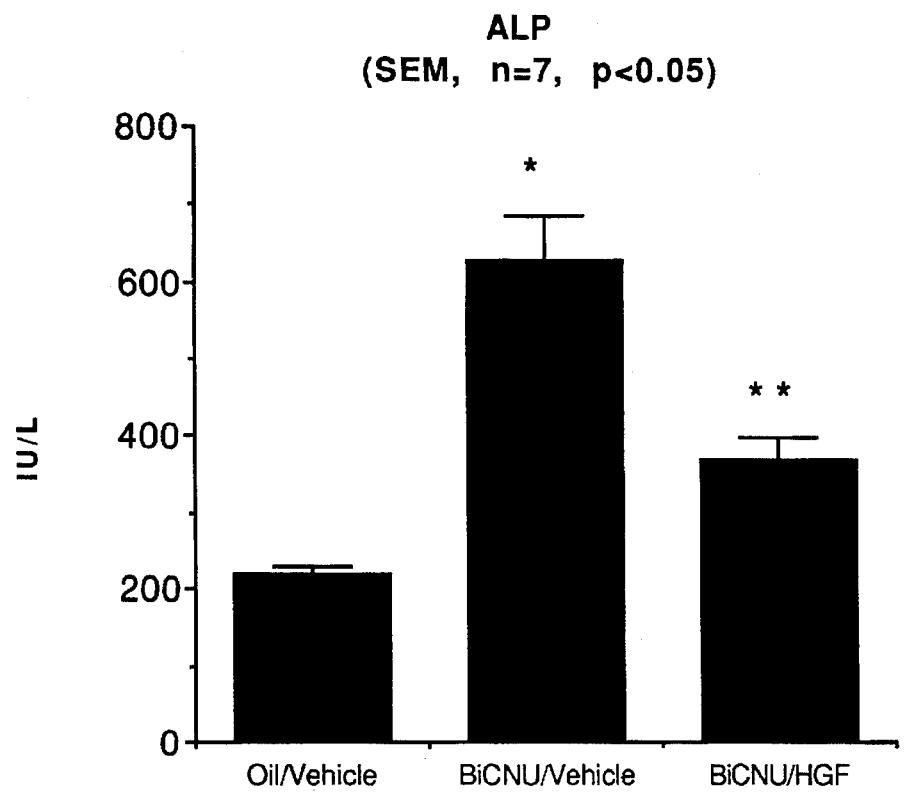
FIGS. 1(a)–1(f) show the alkaline phosphatase (ALP) (FIG. 1(a)), alanine transaminase (ALT) (FIG. 1(b)), aspartate aminotranferase (AST) (FIG. 1(c)), g-glutamine transpeptidase (GGT) (FIG. 1(d)) enzyme levels, total bilirubin (FIG. 1(e)) and amylase (FIG. 1(f)) in rats treated with BiCNU and recombinant human HGF (rHGF) as compared with those treated with BiCNU or vehicle alone. The treatments were performed as described in Example 1.

The phrase "liver damage" is used herein in the broadest sense, and indicates any structural or functional liver injury resulting, directly or indirectly, from internal or external factors or their combinations. Liver damage can be induced by a number of factors including, but not limited to, exposure to hepatotoxic compounds, radiation exposure, mechanical liver injuries, genetic predisposition, viral infections, autoimmune disease, such as, autoimmune chronic hepatitis and as a result of elevated in vivo levels of proteins, such as activin and TGF-β.

Liver damage induced by hepatotoxic compounds includes direct cytotoxicity including drug hypersensitivity reactions, cholestasis, and injury to the vascular endothelium (Sinclair et al., *Textbook of Internal Medicine*, Supra).

A number of hepatotoxic compounds, including certain therapeutics, induce cytotoxicity. Hepatotoxic compounds can produce liver cytotoxicity by direct chemical attack or by the production of a toxic metabolite. Although the exact mechanism of hepatotoxicity is uncertain, the products of reductive metabolism are highly reactive species that bind to cellular macromolecules and cause lipid peroxidation and inactivation of drug metabolizing and other enzymes. The membrane injury provokes release of calcium from mitochondria and smooth endoplasmic reticulum and appears to interfere with the calcium ion pump, which normally prevents cytosolic accumulation of calcium. The deleterious effect on cell metabolism with resultant calcium accumulation, the loss of potassium and enzymes from the cytoplasm, and the loss of essential energy that results from mitochondrial injury all contribute to the necrosis of hepatic tissue.

Many hepatotoxic compounds unpredictably produce liver damage in a small proportion of recipients. In some patients, the liver damage is referred to as a hypersensitivity reaction and is like that of a drug reaction, where the patient presents with fever, rash and eosinophilia and has a recurrence of symptoms upon rechallenge of the drug. In other situations, the mechanism for injury is unknown and may represent aberrant metabolism in susceptible patients that permits the production or accumulation of hepatotoxic metabolites.

Those drugs inducing cytotoxicity by direct chemical attack include the following:

Anesthetics, such as Enflurane, Fluroxene, Halothane, and Methoxyflurane;
Neuropsychotropics, such as, Cocaine, Hydrazides, Methylphenidate, and Tricyclics;
Anticonvulsants, such as, Phenytoin and Valproic acid;
Analgesics, such as, Acetaminophen, Chlorzoxazone, Dantrolene, Diclofenac, Ibuprofen, Indomethacin, Salicylates, Tolmetin, and Zoxazolamine;
Hormones, such as, Acetohexamide, Carbutamide, Glipizide, Metahexamide, Propylthiouracil, Tamoxifen, Diethylstilbestrol;
Antimicrobials, such as, Amphotericin B, Clindamycin, Ketoconazole, Mebendazole, Metronidazole, Oxacillin, Paraaminosalicylic acid, Penicillin, Rifampicin, Sulfonamides, Tetracycline, and Zidovudine;
Cardiovascular drugs, such as, Amiodarone, Dilitiazem, a-Methyldopa, Mexiletine, Hydrazaline, Nicotinic acid, Papaverine, Perhexiline, Procainamide, Quinidine, and Tocainamide; and
Immunosuppressives and Antineoplastics, such as, Asparaginase, Cisplatin, Cyclophosphamide, Dacarbazine, Doxorubicin, Fluorouracil, Methotrexate, Mithramycin, 6-MP, Nitrosoureas, Tamoxifen, Thioguanine, and Vincristine; and
Miscellaneous drugs, such as, Disulfiram, Iodide ion, Oxyphenisatin, Vitamin A and Paraaminobenzoic acid.

Those hepatotoxic compounds producing hypersensitivity reaction in the liver include the following:

Phenytoin, Paraamino salicylic acid, Chlorpromazine, Sulfonamides, Erythromycin estolate, Isoniazid, Halothane, Methyldopa, and Valproic acid.

Hepatotoxic compounds including cholestasis, an arrest in the flow of bile, may take several forms. Centribular cholestasis is accompanied by portal inflammatory changes. Bile duct changes have been reported with some drugs such as erythromycin, while pure canalicular cholestasis is characteristic of other drugs such as the anabolic steroids. Chronic cholestasis has been linked to such drugs as methyltestosterone and estradiol.

Those hepatotoxic compounds inducing cholestatic disease include the following: Contraceptive steroids, androgenic steroids, anabolic steroids, Acetylsalicylic acid, Azathioprine, Benzodiazepine, Chenodeoxycholic acid, Chlordiazepoxide, Erythromycin estolate, Fluphenazine, Furosemide, Griseofulvin, Haloperidol, Imipramine, 6-Mercaptopurine, Methimazole, Methotrexate, Methyldopa, Methylenediamine, Methyltestosterone, Naproxen, Nitrofurantoin, Penicillamine, Perphenazine, Prochlorperazine, Promazine, Thiobendazole, Thioridazine, Tolbutamide, Trimethoprimsulfamethoxazole, Arsenic, Copper, and Paraquat.

Some drugs, although primarily cholestatic, can also produce hepatoxicity, and therefore the liver injury they cause is mixed. The drugs causing mixed liver injury include, for example, the following:

Chlorpromazine, Phenylbutazone, Halothane, Chlordiazepoxide, Diazepam, Allopurinol, Phenobarbital, Naproxen, Propylthiouracil, Chloramphenicol, Trimethoprimsulfamethoxazxole, Amrinone, Disopyramide, Azathioprine, Cimetidine, and Ranitidine.

Vascular lesions of the liver, including thrombosis of the hepatic veins, occlusion of the hepatic venules or veno occlusive disease (VOD), and peliosis hepatitis, can be produced by drugs. In addition, lesions including sinusoidal dilation, perisinusoidal fibrosis, and hepatoportal selerosis can occur. Midzonal and pericentral sinusoidal dilatation was first reported as a complication of oral contraceptive therapy. Peliosis hepatitis is a condition consisting of large blood-filled cavities that results from leakage of red blood cells through the endothelial barrier, followed by perisinusoidal fibrosis. It has been described in patients taking oral contraceptives, anabolic steroids, azathioprine and danazol. Injury and occlusion of the central hepatic venules is also known to be related to the ingestion of pyrrolizidine alkaloids, such as bush teas. The initial lesion is central necrosis accompanied by a progressive decrease in venule caliber. All of these lesions may be only partially reversible when the drug is stopped and cirrhosis can develop.

Several types of benign and malignant hepatic neoplasm can result from the administration of hepatotoxic compounds. Adenomas, a lesion restricted to women in the childbearing years, is related to the use of contraceptive steroids and the risk increases with duration of use. Hepatocellular carcinoma may also be seen in patients taking androgenic hormones for aplastic anemia or hypopituitarism.

Hepatotoxic compounds known to cause hepatic liesons include the following: Contraceptive steroids, Pyrriolizidine alkaloids, Urethane, Azathioprine, 6-Mercaptopurine, 6-Thioguanine, Mitomycin, BCNU, Vincristine, Adriamycin, Intravenous Vitamin E, Anabolic-androgenic steroids, Azathioprine, Medroxyprogesterone acetate, Estrone sulfate, Tamoxifen, inorganic arsenicals, Thorium dioxide, Vitamin A, methotrexate, Methylamphetamine hydrochloride, Vitamin A, Corticosteroids, Thorium dioxide, and Radium therapy.

Liver damage caused by other factors usually takes similar forms.

Liver damage, whether caused by the hepatotoxicity of a compound, radiation therapy, genetic predisposition, mechanical injury or any combination of such and other factors, can be detected by several means. Biochemical tests have been used clinically for many years as the standard measure of hepatotoxicity. Most biochemical tests generally fall into two categories: tests which measure specific liver markers, for example, prothrombin clotting time, and/or hepatic blood flow, or tests which analyze serum markers, for detection of necrosis, cholestasis, progressive fibrogenesis, or hepatoma (Cornelius, C. in Hepatotoxicology, Meeks et al. eds., pgs. 181–185 (1991)). The importance of such tests lies in their simplicity and the fact that they are non-invasive. The rationale for the use of serum enzymes in assessing liver damage is that these enzymes, normally contained in the liver cells, gain entry into the general circulation when liver cells are injured. Elevated serum enzyme activity suggests nercrosis and/or cholestasis. Elevated levels of serum bilirubin conjugates suggest intra or extra hepatic cholestasis. However, there are certain limitations for the use of serum enzyme levels as single means of diagnosing liver injury. Serum enzyme levels may increase as a result of leakage from cells with altered permeability due to systemic effects of an agent rather than specific liver injury caused by a chemical. Histopathological examination of the liver is the next logical step in identifying and quantitating the nature and extent of liver injury.

The serum enzymes as markers of liver injury can be divided into four groups based on specificity and sensitivity to liver damage (Kodavanti, et al. in Hepatotoxicology, Supra, pgs. 241–244).

Group I: these enzymes indicate more selectively hepatic cholestasis when elevated, e.g. alkaline phosphatase (AP), 5'-nucleotidase (5'-ND), and a-glutamyl transpeptidase (G-GT) and leucine aminopeptidase (LAP).

Group II: These enzymes indicate parenchymal injury when elevated, e.g., aspartate transaminase (AST), alanine transaminase (ALT), fructose-1,6-diphosphate aldolase (ALD), lactate dehydrogenase (LDH), isocitrate dehydrogenase (ICDH), ornithine-carbamoyl-transferase (OCT), and sorbitol dehydrogenase (SDH) arginase and guanase.

Group III: These enzymes represent injury of other tissue when elevated e.g., creatine phosphokinase (CPK).

Group IV: These enzymes are depressed in hepatic injury, e.g., cholinesterase (ChE).

Other serum markers include, procollagen type III peptide levels (PIIIP) to assess if hepatic fibrogenesis is active; ammonia blood levels in hepatoencephalopathies; ligand in levels in necrosis and hepatoma; hyaluronate levels due to hepatic endothelial cell damage; a-1-fetoprotein (AFP) levels to detect hepatoma; carcinoembryonic antigen (CEA) levels to detect cancer metastasis to the liver; elevations of antibodies against a variety of cellular components, such as, mitochondrial, and nuclear and specific liver membrane protein; and detection of proteins, such as, albumin, globin, amino acids, cholestrol, and other lipids. Also, biochemical analysis of a variety of minerals, metabolites, and enzymes obtained from liver biopsies can be useful in studying specific biochemical defects in inherited, acquired, and experimentally induced liver disorders.

Liver function tests can be performed to assess liver injury. Liver function tests include the following:

Group I assessment of hepatic clearance of organic anions, such as, bilirubin, indocyanine green (ICG), sulfobromophthalein (BSP) and bile acids;

Group II assessment of hepatic blood flow by measurements of galactose and ICG clearance; and Group III assessment of hepatic microsomal function, through the use of the aminopyrine breath test and caffeine clearance test.

For example, serum bilirubin can be measured to confirm the presence and severity of jaundice and to determine the extent of hyperbilirubinemia, as seen in parenchymal liver disease. Aminotransferase (transaminase) elevations reflect the severity of active hepatocellular damage, while alkaline phosphatase elevations are found with cholestasis and hepatic infiltrates (Isselbacher, K. and Podolsky, D. in Hartison's *Principles of Internal Medicine*, 12th edition, Wilson et al. eds., 2: 1301–1308 (1991)).

Methods for performing serum enzyme analysis are known in the art and are, for example, described in Kodavanti, et al., Supra.

Because extensive liver injury may lead to decreased blood levels of albumin, prothrombin, fibrinogen, and other proteins synthesized exclusively by hepatocytes, these protein levels may be measure as indicators of liver injury. In contrast to measurements of serum enzymes, serum protein levels reflect liver synthetic function rather than just cell injury (Podolsky, D. *Principles of Internal Medicine*, 12th edition, Wilson et al. eds., 2: 1308–1311 (1991)).

In many patients, computed tomography (CT), ultrasound, scintiscans, or liver biopsy may be needed to determine the nature of the liver disease (Isselbacher, K, Supra and Friedman, L. and Needleman, L. in Harrison's *Principles of Internal Medicine*, 12th edition, Wilson et al. eds., 2: 1303–1307 (1991)).

The term "prevention" as used in the context of the present invention includes the complete or partial blocking of the occurrence of anticipated liver damage and the interception or moderation of the progress of liver damage already occurred. Whereas it is foreseen that existing liver damage may be completely or partially reversed, this is not a requirement under this definition.

The term "preventatively effective amount" include those patients who are anticipated to be exposed to or who have been exposed to any factor known to have the potential of inducing liver damage. This includes exposure to hepatotoxic compounds (whether as part of a therapy or due to accidental exposure), in doses conventionally considered safe or in doses conventionally considered unsafe, radiation, or any clinical therapy useful in the treatment of a disease, wherein said clinical therapy is known to induce liver damage. The definition further includes actual or potential sustained liver injury through physical trauma including, blunt trauma, gunshot wounds, or surgery. Patients at risk of developing liver damage include those patients having inborn errors of metabolism and who are genetically predisposed to induction of liver damage, or those mammalian patients susceptible to liver damage due to other risk factors including genetic factors, age, sex, nutritional status, exposure to other drugs, and systemic diseases. Patients at risk of developing liver damage also includes those patients who are anticipated to be exposed to or who have been exposed to viruses such as hepatitis A, B, C, D, and E, or autoimmune chronic hepatitis.

"Radiation" as used herein refers to exposure to x-rays or any other rays known to have hepatotoxic side-effects, including radiation therapy and accidental exposure.

In the context of the present invention the term "hepatocyte growth factor" or "HGF" is used to refer to a native hepatocyte growth factor or any fragment or derivative thereof capable of the prevention of the establishment or of the progress of liver damage as determined in standard tests as hereinabove described. The term specifically includes human and non-human, such as rat HGF, in mature, pre, pre-pro, or pro forms, purified from natural source, chemically synthesized or recombinantly produced, and their derivatives.

The term "human hepatocyte growth factor" or "hHGF" refers to a polypeptide encoded by the cDNA sequence published by Miyazawa, et al., Supra, or Nakamura et al., *Nature*, Supra, including its single- and double-chain, mature, pre, pre-pro, and pro forms, purified from natural source, chemically synthesized or recombinantly produced, or any fragment or derivative thereof, retaining the qualitative ability to prevent the establishment or of the progress of liver damage as determined by any of the standard tests described above.

The "native" "wild-type" hHGF cDNA encodes a 728 amino acids polypeptide (pre-pro hHGF) having a molecular mass ($M_r$) of about 82,000, and a heterodimeric structure, composed of a large a-subunit of 440 amino acids ($M_r$ 69,000) and a small β-subunit of 234 amino acids ($M_r$ 34,000). The nucleotide sequence of hEGF cDNA reveals that both the a- and the β-chains are contained in a single open reading frame coding for a pre-pro precursor protein. In the predicted primary structure of mature hHGF, an interchain S-S bridge is formed between Cys 487 of the a-chain and Cys 604 in the β-chain (see Nakamura et al., *Nature*, Supra). The N-terminus of the a-chain is preceded by 54 amino acids, starting with a methionine group. This segment includes a signal sequence and the prosequence. The a-chain starts at amino acid (aa) 55, and contains four Kringle domains. The Kringle 1 domain extends from about aa 128 to about aa 206, the Kringle 2 domain is between about aa 211 and about aa 288, the Kringle 3 domain is defined as extending from about aa 303 to about aa 383, and the Kringle 4 domain extends from about aa 391 to about aa 464 of the a-chain. It will be understood that the definition of the various Kringle domains is based on their homology with kringle-like domains of other proteins (prothrombin, plasminogen), therefore, the above limits are only approximate. The HGF β-chain includes a serine-protease like domain. HGF contains four putative glycosylation sites, which are located at positions 294 and 402 of the a-chain and at positions 566 and 653 of the β-chain. The sequences reported for native hHGF by Miyazawa et al. and Nakamura et al. differ in 14 amino acids. The reason for the differences is not entirely clear; polymorphism or cloning artifacts are among the possibilities. Both sequences are specifically encompassed by the term "native hHGF" as defined for the purpose of the present invention. The term specifically includes "delta5 hHGF", a variant in which 5 amino acids are deleted in the first kringle domain of native human hHGF, which was first identified and described by Seki et al., Supra.

It is believed that any HGF molecule exhibiting HGF biological activity is suitable for the purpose of the present invention. Accordingly, the testing of HGF biological activity is indicative of the utility of an HGF derivative as a liver damage preventative agent.

For purposes herein, "activin antagonist" refers to any molecule that inhibits the activity of activin in causing death of hepatocytes. As used herein, "activin" refers to homo- or heterodimers of β chains of inhibin, prepro forms, and pro forms, together with glycosylation variants thereof, whether in native form or synthetic or recombinant form. Activin A refers to activin with the two chains of $β_A$. Activin AB refers to activin with the chains $β_A$ and $β_B$. Activin B refers to activin with the two chains of $β_B$.

Typically the activin antagonist is a protein that binds to an active site of activin and includes, e.g., follistatin as described in Esch et al., *Mol. Endocrinol.*, 1: 849–855 [(1987); Shimasaki et al., *Proc. Natl. Acad. Sci. USA*, 85: 4218–4222 (1988); Shimasaki et al., *Biochem. Biophys. Res. Comm.*, 152: 717–723 (1988); Shimasaki et al., *Mol. Endocrinol.*, 3: 651–659 (1989); Ueno et al., *Proc. Natl. Acad. Sci. USA*, 84: 8282 (1987); Nakamura et al., *Science*, 247: 836 (1990); Shimonaka et al., *Endocrinology*, 128: 3313 (1991).

In addition, the antagonist may be a non-proteinaceous small molecule that acts as an activin antagonist. Such molecules can be screened by their ability to inhibit the action of activin in promoting liver injury or liver cell death using the assays described above and in the examples, such as the MTT assay.

The definition of antagonist also includes an anti-activin antibody, whether polyclonal or monoclonal. Monoclonal antibodies specific for human recombinant activin A or B can be produced as described by Corrigan et al., *Endocrinology*, 128: 1682 (1991). Briefly, inbred HPG-hypogonadal mice (Jackson Laboratories, Wilmington, Mass.) are hyperimmunized in the hind footpad with purified recombinant activin A, B, or AB. Cells harvested from the draining lymph nodes are then fused with the mouse myeloma line X63-Ag8.653. Kearney et al., *J. Immunol.*, 123: 1548 (1979). The fusions are screened for reactivity and specificity in an ELISA using recombinant human activin A, activin B, activin AB, and inhibin A as coat proteins. Wong et al., *Clinical Chemistry*, 36: 192 (1990). Parental hybridomas that react specifically with either recombinant human activin A, B, or AB are cloned by limiting dilution. Ascites fluids are produced in Balb/c nu/nu mice, and antibody is purified by protein A-sepharose affinity chromatography (Repligen Corp., Cambridge, Mass.) according to established procedures (Goding, *J. Immunol. Meth.*, 20: 241 [1978]; Ey et al., *Immunochemistry*, 15: 429 [1978]), and stored under sterile conditions in phosphate buffered saline (PBS) at 4° C. Antibodies against activin or activin peptides that may also be suitable herein, although they may also cross-react with inhibin to some degree, include those described by Lofgren et al., *J. Immunoassay*, 12: 565 (1991); Shintani et al., *J. Immunol. Meth.*, 137: 267 (1991); Groome and Lawrence, *Hybridoma*, 10: 309 (1991); Groome, *J. Immunol. Meth.*, 145: 65–69 (1992); and Schwall et al., *Non-Radiometric Assays: Technology and Application in Polypeptide and Steroid Hormone Detection*, pages 205–220 (Alan R. Liss, Inc., 1988).

Another suitable activin antagonist herein is an inhibitor of activin such as that described in Shiozaki et al., supra, or a soluble form of an activin receptor.

Examples of suitable activin receptors include that described in copending U.S. Ser. No. 07/716,826 filed 19 Jun. 1991, the disclosure of which is incorporated by reference. Briefly, the receptor is described as not binding to TGF-β, having a molecular weight on reduced 10% SDS-PAGE of 135–150 kd, and having an N-terminal sequence of:

ValLeuThrGluGluThrGluIleIleMetProThrProLysProGluLeuXaaAlaXaa wherein Xaa indicates an unknown amino acid. To the extent that the "activin receptor" described in Mathews and Vale, *Cell*, 65: 1–20 [1991] and Mathews et al., *Science*, 255: 1702–1705 (1992) blocks activin biological activity in hepatocytes, it is included herein. Activin receptors have also been reported by Attisano et al., *Cell*, 68: 97–108 [1992] and Kondo et al., *Biochem. Biophys. Res. Comm.*, 181: 684–690 [1991].

The definition of activin antagonists also includes fragments of the above molecules that contain the active site needed to block activin activity, including F(ab) and Fc fragments of antibodies, etc.

Efficacy in preventing cell death in certain liver diseases is seen with a treatment regimen that employs an activin antagonist administered in an effective dose.

Examples of TGF-β antagonists include antibodies to TGF-β such as those described in Lucas et al., *J. Immunol.*, 145: 1415–1422 (1990); Dasch et al., *J. Immunol.*, 142: 1536–1541 (1989); Ellingsworth et al., *J. Biol. Chem.*, 261: 12362–12367 (1986); Cheifetz et al., *Cell*, 48: 409–415 (1987); Florini et al., *J. Biol. Chem.*, 261, 16509–16513 (1986); Roberts et al., *Proc. Natl. Acad. Sci. USA*, 83: 4167–4171 (1986); Assoian and Sporn, *J. Cell Biol.*, 102: 12178–1223 (1986); Ellingsworth et al., *Cell. Immunol.*, 114: 41 (1988); Flanders et al., *Biochemistry*, 27: 739 (1988); Keski-Oja et al., *Cancer Res.*, 47: 6451 (1988);

Danielpour and Sporn, *J. Cell Biochem.*, 13B: 84 (1989); and Danielpour et al., *J. Cell Physiol.*, 138: 79–86 (1989).

Additional TGF-β antagonists that are suitable include non-proteinaceous small molecules that act as a TGF-β antagonist in blocking the ability of TGF-β to cause hepatic injury or hepatocyte death, screened by, e.g., the MTT test, and a soluble form of the TGF-β receptor or TGF-β binding protein of any type, as described, for example, in Lin et al., *Cell*, 68: 775–785 (1992); Lin et al., *J. Cell Biochem. Suppl.*, 16 Part B, p. 125 (1992); Wang et al., *Cell*, 67: 797–805 (1991); EP 369,861 published 23 May 1990; Wang et al., *J. Cell Biochem. Suppl.*, 16, part B, p. 129 (1992); Lopez-Casillas et al., *Cell*, 67: 785–795 (1991); O'Grady et al., *J. Biol. Chem.*, 266: 8583–8589 (1991); Segarini et al., *J. Biol. Chem.*, 267: 1048–1053 (1992); MacKay et al., *J. Biol. Chem.*, 265: 9351–9356 (1990); Cheifetz and Massague, *J. Biol. Chem.*, 266: 20767–20772 (1991); Cheifetz and Massague, *J. Cell Biochem. Suppl.*, 16, part B, p. 121 (1992); Ichijo et al., *J. Biol. Chem.*, 266: 22459–22464 (1991); Borisuth et al., *Invest. Ophthal. and Vis. Sci.*, 33: 596–603 (1992); Mitchell and O'Connor-McCourt, *J. Cell Biol.*, 115: 3, Part 2, p. 265A (1991).

For recent reviews of TGF-β receptors, see Segarini, "TGF-βReceptors," *Clinical Applications of TGF-β* (Wiley, Chichester [Ciba Foundation Symposium 157], p. 29–50, 1991), and Massague et al., *Annals NY Acad. Sci.*, p. 59–72, 1990.

If antibodies to activin or TGF-β are employed as the antagonist, they are prepared by any suitable technique. For example, activin or immunogenic fragments of activin may be used to induce the formation of anti-activin antibodies, which are identified by routine screening. Similarly, TGF-β or immunogenic fragments of TGF-β may be used to induce the formation of anti-TGF-β antibodies which are identified by routine screening. Such antibodies may either be polyclonal or monoclonal antibodies, or antigen-binding fragments of such antibodies (such as, for example, F(ab) or F(ab)$_2$ fragments). The antibodies are monovalent or polyvalent for activin. An activin antagonist or mixtures thereof or with another suitable adjuvant therapeutic agent is generally used in a single course of therapy.

Polyclonal antibodies to activin or TGF-β generally are raised in animals by multiple subcutaneous (s.c.) or intraperitoneal (i.p.) injections of the activin polypeptide together with an adjuvant. It may be useful to conjugate the activin antigen polypeptide (including its chains and fragments containing the target amino acid sequence) to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups.

The route and schedule for antibody stimulation of the host animal or cultured antibody-producing cells therefrom are generally in keeping with established and conventional techniques for antibody stimulation and production. While mice are frequently employed as the test model, it is contemplated that any mammalian subject including human subjects or antibody-producing cells obtained therefrom can be manipulated according to the processes of this invention to serve as the basis for production of mammalian, including human, hybrid cell lines.

Animals are typically immunized against the immunogenic conjugates or derivatives by combining 1 mg or 1 μg of conjugate (for rabbits or mice, respectively) with 3 volumes of Freund's complete adjuvant and injecting the solution intradermally at multiple sites. One month later the animals are boosted with ⅕ to ¹⁄₁₀ the original amount of conjugate in Freund's incomplete adjuvant (or other suitable adjuvant) by subcutaneous injection at multiple sites. Seven to 14 days later animals are bled and the serum is assayed for antibody titer. Animals are boosted until the titer plateaus. Preferably, the animal is boosted with the conjugate of the same activin polypeptide, but conjugated to a different protein and/or through a different cross-linking agent. Conjugates also can be made in recombinant cell culture as protein fusions. Also, aggregating agents such as alum are used to enhance the immune response.

Monoclonal antibodies are prepared by recovering immune cells—typically spleen cells or lymphocytes from lymph node tissue—from immunized animals and immortalizing the cells in conventional fashion, e.g., by fusion with myeloma cells or by Epstein-Barr (EB)-virus transformation and screening for clones expressing the desired antibody. The hybridoma technique described originally by Kohler and Milstein, *Eur. J. Immunol.*, 6: 511 (1976) and also described by Hammerling et al., In: *Monoclonal Antibodies and T-Cell Hybridomas*, Elsevier, N.Y., pp. 563–681 (1981) has been widely applied to produce hybrid cell lines that secrete high levels of monoclonal antibodies against many specific antigens.

It is possible to fuse cells of one species with another. However, it is preferable that the source of the immunized antibody-producing cells and the myeloma be from the same species.

The hybrid cell lines can be maintained in culture in vitro in cell culture media. The cell lines producing the antibodies can be selected and/or maintained in a composition comprising the continuous cell line in hypoxanthine-aminopterin thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody.

The secreted antibody is recovered from tissue culture supernatant by conventional methods such as precipitation, ion-exchange chromatography, affinity chromatography, or the like. The antibodies described herein are also recovered from hybridoma cell cultures by conventional methods for purification of IgG or IgM, as the case may be, that heretofore have been used to purify these immunoglobulins from pooled plasma, e.g., ethanol or polyethylene glycol precipitation procedures. The purified antibodies are sterile filtered.

While routinely mouse monoclonal antibodies are used, the invention is not so limited; in fact, human antibodies may be used and may prove to be preferable. Such antibodies can be obtained by using human hybridomas (Cote et al., *Monoclonal Antibodies and Cancer Therapy*, Alan R. Liss, p. 77 [1985]). In fact, according to the invention, techniques developed for the production of chimeric antibodies (Morrison et al., *Proc. Natl. Acad. Sci.*, 81: 6851 [1984]; Neuberger et al., *Nature*, 312: 604 [1984]; Takeda et al., *Nature*, 314: 452 [1985]; EP 184,187: EP 171,496: EP 173,494; PCT WO 86/01533; Shaw et al., *J. Nat. Canc. Inst.*, 80: 1553–1559 [1988]; Morrison, *Science*, 229: 1202–1207 [1985]; Oi et al., *BioTechniques*, 4: 214 [1986]) by splicing the genes from a mouse antibody molecule of appropriate antigen specificity together with genes from a human antibody molecule of appropriate biological activity (such as ability to block activin's activity in hepatocytes) can be used; such antibodies are within the scope of this invention.

Techniques for creating recombinant DNA versions of the antigen-binding regions of antibody molecules (known as F(ab) fragments), which bypass the generation of monoclonal antibodies, are encompassed within the practice of this invention. One extracts antibody-specific messenger RNA molecules from immune system cells taken from an immunized animal, transcribes these into complementary DNA (cDNA), and clones the cDNA into a bacterial expression system. One example of such a technique suitable for the practice of this invention was developed by researchers at Scripps/Stratagene, and incorporates a proprietary bacteriophage lambda vector system that contains a leader sequence that causes the expressed F(ab) protein to migrate to the periplasmic space (between the bacterial cell membrane and the cell wall) or to be secreted. One can rapidly generate and screen great numbers of functional F(ab) fragments for those that bind the antigen. Such activin-binding molecules (F(ab) fragments with specificity for the activin polypeptide) are specifically encompassed within the term "antibody" as it is defined, discussed, and claimed herein.

The terms "biological activity", "biologically active", "activity" and "active" refer to any mitogenic, motogenic or morphogenic activities exhibited by wild-type human HGF. The HGF biological activity may, for example, be determined in an in vitro or in vivo assay of hepatocyte growth promotion. Adult rat hepatocytes in primary culture have been extensively used to search for factors that regulate hepatocyte proliferation. Accordingly, the mitogenic effect of an HGF variant can be conveniently determined in an assay suitable for testing the ability of an HGF molecule to induce DNA synthesis of rat hepatocytes in primary cultures. Adult rat hepatocytes in primary culture have been extensively used to search for factors that regulate hepatocyte proliferation, accordingly, techniques for isolating and culturing rat hepatocytes are well known in the art. Human hepatocytes can, for example, be obtained from whole liver perfusion on organs deemed unacceptable for transplantation, pare-downs of adult livers used for transplantation in children, fetal livers and liver remnants removed at surgery for other indications. Human hepatocytes can be cultured similarly to the methods established for preparing primary cultures of normal rat hepatocytes.

Hepatocyte DNA synthesis can, for example, be assayed by measuring incorporation of [$^3$H]thymidine into DNA, with appropriate hydroxyurea controls for replicative synthesis. Nuclear labelling is confirmed by autoradiography. A method for measuring hepatocyte DNA synthesis in primary culture of hepatocytes with or without aphidicolin is described by Nakamura et al., in *Biochem. Biophys. Res. Comm.* 122(3): 140–1459 (1984), and in *J. Biochem.* 94: 1029–1035 (1983).

The effect of HGF on hepatocyte growth can also be tested in vivo in animal models of liver dysfunction and regeneration, such as in rats following partial hepatectomy, or carbon tetrachloride caused hepatic injury, in D-galactosamine induced acute liver failure models, etc. According to a suitable protocol, a liver poison, e.g. a-naphthylisothiocyanate (ANIT) is administered to rats in a predetermined concentration capable of causing reproducible significant elevation of liver enzyme and bilirubin levels. The rats are then treated with the HGF to be tested, sacrificed and the liver enzyme and bilirubin levels are determined. The livers are additionally observed for hepatic lesions.

The effect of HGF on hepatocyte growth and prevention of liver damage can also be tested in vivo in transgenic animal models, such as described in U.S. Pat. No. 5,087,571 issued Mar. 22, 1988. According to suitable protocol, transgenic animals subject to liver disease or liver damage are treated with the HGF to be tested or HGF co-administered with a therapeutic useful in the treatment of disease, sacrificed and the liver enzyme and bilirubin levels determined. The livers are additionally observed for hepatic lesions.

One colorimetric test useful in determining if cell death has occurred is to measure reduction of MTT, as described by Carmichael et al., *Cancer Res.*, 47: 936–942 (1987). In this assay, if the cell is alive, its mitochondria will take up the dye MTT, resulting in a color change from yellow to purple. If the cell is dead, no color change will result.

The term "derivative" is used to define amino acid sequence and glycosylation variants, and covalent modifications of a native hepatocyte growth factor.

The terms "amino acid" and "amino acids" refer to all naturally occurring L-a-amino acids. This definition is meant to include norleucine, ornithine, and homocysteine. The amino acids are identified by either the single-letter or three-letter designations:

Asp D aspartic acid
Thr T threonine
Ser S serine
Glu E glutamic acid
Pro P proline
Gly G glycine
Ala A alanine
Cys C cysteine
Val V valine
Met M methionine
Ile I isoleucine
Leu L leucine
Tyr Y tyrosine
Phe F phenylalanine
His H histidine
Lys K lysine
Arg R arginine
Trp W tryptophan
Gln Q glutamine
Asn N asparagine These amino acids may be classified according to the chemical composition and properties of their side chains. They are broadly classified into two groups, charged and uncharged. Each of these groups is divided into subgroups to classify the amino acids more accurately:

I. Charged Amino Acids

Acidic Residues: aspartic acid, glutamic acid
Basic Residues: lysine, arginine, histidine II. Uncharged Amino Acids Hydrophilic Residues: serine, threonine, asparagine, glutamine
Aliphatic Residues: glycine, alanine, valine, leucine, isoleucine
Non-polar Residues: cysteine, methionine, proline
Aromatic Residues: phenylalanine, tyrosine, tryptophan The terms "alteration", "amino acid alteration", "variant" and "amino acid sequence variant" refer to HGF molecules with some differences in their amino acid sequences as compared to a native HGF, such as to native hHGF.

Ordinarily, the variants will possess at least about 80% homology with those domains of wild-type (human) HGF that are retained in their structure, and preferably, they will be at least about 90% homologous with such domains. Methods for the alignment of amino acid sequences for maximum homology are well known in the art. Amino acid sequence variants of HGF polypeptides may be naturally occurring alleles (which will not require manipulation of the HGF DNA) or predetermined mutant forms made by mutating the DNA, either to arrive to an allele or a variant not found in nature, provided that such variants maintain the biological activity in kind of native human HGF. Such mutations typically involve substitution, deletion and/or insertion of one or more amino acids in the native amino acid sequence. The amino acid changes also may result in further modifications of HGF upon expression in recombinant hosts, e.g. introducing or moving sites of glycosylation. It will be understood that natural allelic variations exist and can occur among individuals, as demonstrated by one or more amino acid differences in the amino acid sequence of each individual.

Substitutional HGF variants are those that have at least one amino acid residue in the corresponding wild-type HGF sequence removed and a different amino acid inserted in its place at the same position. The substitutions may be single, where only one amino acid in the molecule has been substituted, or they may be multiple, where two or more amino acids have been substituted in the same molecule.

Substantial changes in the activity of the HGF molecule may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the HGF molecule would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional HGF variants are those with one or more amino acids inserted immediately adjacent to an amino acid at a particular position in the wild-type HGF molecule. Immediately adjacent to an amino acid means connected to either the a-carboxy or a-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those with one or more amino acids in the wild-type HGF molecule removed. Ordinarily, deletional variants will have one or two amino acids deleted in a particular region of the HGF molecule.

The notations to describe hHGF amino acid sequence variants are described below. The location of a particular amino acid in the polypeptide chain of hHGF is identified by a number. The number refers to the amino acid position in the amino acid sequence of the mature, wild-type human HGF polypeptide as disclosed in Miyazawa et al., 1989, Supra. Similarly positioned residues in hHGF variants are designated by these numbers even though the actual residue number is not so numbered due to deletions or insertions in the molecule. This will occur, for example, with site-directed deletional or insertional variants. The amino acids are identified using the one-letter code. Substituted amino acids are designated by identifying the wild-type amino acid on the left side of the number denoting the position in the polypeptide chain of that amino acid, and identifying the substituted amino acid on the right side of the number.

For example, replacement of the amino acid arginine (R) by glutamic acid (E) at amino acid position 494 of the wild-type hHGF molecule yields a hHGF variant designated R494E hHGF. Similarly, the hHGF variant obtained by substitution of serine (S) for tyrosine (Y) at amino acid position 673 and serine (S) for valine (V) at amino acid position 692 of the wild-type hHGF molecule is designated Y673S, V692S huHGF.

Deletional variants are identified by indicating the amino acid residue and position at either end of the deletion, inclusive, and placing the Greek letter delta, "Δ", to the left of the indicated amino acids. Deletion of a single amino acid is indicated by placing Δ to the left of the single letter code and number indicating the position of the deleted amino acid.

Insertional variants are designated by the use of brackets "[]" around the inserted amino acids, and the location of the insertion is denoted by indicating the position of the amino acid on either side of the insertion.

Amino acid variants of hGHF are known in the art. Single-chain variants of HGF are described in U.S. Ser. No. 07/884,811 filed 18 May 1992. The single-chain variants are resistant to proteolytic cleavage by enzymes that are capable of in vivo conversion of the single-chain HGF proenzyme into its two-chain form. Absent alterations, the proteolytic cleavage takes place between Arg494 and Val495 of the wild-type huHGF sequence. In general, the substitution of smaller, apolar or acidic amino acids for arginine at this position is believed to yield single-chain HGF variants.

Protease domain variants of HGF are described in U.S. Ser. No. 07/885,871. Desirable HGF amino acid variants are those that have retained or enhanced receptor binding affinity and substantially retained or increased biological activity as compared to the corresponding wild-type HGF (HGF agonists).

These and further HGF amino acid sequence variants can be prepared by methods known in the art, such as site-directed mutagenesis of the encoding DNA sequence, chemical synthesis, etc.

Whereas any technique known in the art can be used to perform site-directed mutagenesis, e.g. as disclosed in Sambrook et al. (*Molecular Cloning: A Laboratory Manual*, second edition, Cold Spring Harbor Laboratory Press, New York (1989)), oligonucleotide-directed mutagenesis is the preferred method for preparing the HGF variants of this invention. This method, which is well known in the art (Adelman et al. *DNA*, 2:183 (1983), Sambrook et al., Supra), is particularly suitable for making substitution variants, it may also be used to conveniently prepare deletion and insertion variants.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981). These phage are readily commercially available and their use is generally well known to those skilled in the art. Alternatively, plasmid vectors that contain a single-stranded phage origin of replication (Veira et al., *Meth. Enzymol,* 153:3 (1987)) may be employed to obtain single-stranded DNA.

The oligonucleotides are readily synthesized using techniques well known in the art such as that described by Crea et al., *Proc. Nat'l. Acad. Sci. USA* 75:5765 (1978), or Kunkel et al., *Methods in Enzymol,* 154 367–382 (1987).

Mutants with more than one amino acid substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant.

Another method for making mutations in the DNA sequence encoding wild-type HGF or a variant molecule known in the art, involves cleaving the DNA sequence encoding the starting HGF molecule at the appropriate position by digestion with restriction enzymes, recovering the properly cleaved DNA, synthesizing an oligonucleotide encoding the desired amino acid sequence and flanking regions such as polylinkers with blunt ends (or, instead of polylinkers, digesting the synthetic oligonucleotide with the restriction enzymes also used to cleave the HGF encoding DNA, thereby creating cohesive termini), and ligating the synthetic DNA into the remainder of the HGF encoding structural gene.

PCR mutagenesis is also suitable for making the HGF variants of the present invention, for example, as described in U.S. Pat. No. 4,683,195 issued 28 Jul. 1987 and in *Current Protocols in Molecular Biology,* Ausubel et al., eds. Greene Publishing Associates and Wiley-Interscience, Volume 2, Chapter 15, 1991. While the following discussion refers to DNA, it is understood that the technique also find application with RNA. The PCR technique generally refers to the following procedure. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone. If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer or performing a second PCR with different mutant primers and ligating the two resulting PCR fragments simultaneously to the vector fragment in a three (or more)-part ligation.

The cDNA encoding such HGF variants is then inserted into a replicable vector for further cloning or expression.

Suitable vectors are prepared using standard recombinant DNA procedures. Isolated plasmids and DNA fragments are cleaved, tailored, and ligated together in a specific order to generate the desired vectors.

After ligation, the vector with the foreign gene now inserted is transformed into a suitable host cell. The transformed cells are selected by growth on an antibiotic, commonly tetracycline (tet) or ampicillin (amp), to which they are rendered resistant due to the presence of tet and/or amp resistance genes on the vector. If the ligation mixture has been transformed into a eukaryotic host cell, transformed cells may be selected by the DHFR/MTX system. The transformed cells are grown in culture and the plasmid DNA (plasmid refers to the vector ligated to the foreign gene of interest) is then isolated. This plasmid DNA is then analyzed by restriction mapping and/or DNA sequencing. DNA sequencing is generally performed by either the method of Messing et al., *Nucleic Acids Res.* 9:309 (1981) or by the method of Maxam et al., *Methods of Enzymology* 65:499 (1980).

Prokaryotes are the preferred host cells for the initial cloning steps of HGF. They are particularly useful for rapid production of large amounts of DNA, for production of single-stranded DNA templates used for site-directed mutagenesis, for screening many mutants simultaneously, and for DNA sequencing of the mutants generated. For expressing HGF eukaryotic hosts, such as eukaryotic microbes (yeast) and multicellular organisms (mammalian cell cultures) may also be used. Examples of prokaryotes, e.g. *E. coli,* eukaryotic microorganisms and multicellular cell cultures, and expression vectors, suitable for use in producing HGF are, for example, those disclosed in WO 90/02798 (published 22 Mar. 1990).

Cloning and expression methodologies are well known in the art and are, for example, disclosed in the foregoing published PCT patent application (WO 90/02798).

If mammalian cells are used as host cells, transfection generally is carried out by the calcium phosphate precipitation method as described by Graham and Van der Eb, *Virology,* 52: 546 (1978). However, other methods for introducing DNA into cells such as nuclear injection, electroporation, or protoplast fusion are also suitably used.

If yeast are used as the host, transfection is generally accomplished using polyethylene glycol, as taught by Hinnen, *Proc. Natl. Acad. Sci. U.S.A.* 75: 1929–1933 (1978).

If prokaryotic cells or cells that contain substantial cell wall constructions are used, the preferred method of transfection is calcium treatment using calcium as described by Cohen et al., *Proc. Natl. Acad. Sci.* (*USA*) 69: 2110 (1972), or more recently electroporation.

HGF preferably is recovered from the culture medium as a secreted protein, although it also may be recovered from host cell lysates when directly expressed without a secretory signal. When the variant is expressed in a recombinant cell other than one of human origin, the variant is thus completely free of proteins of human origin. However, it is necessary to purify the variant from recombinant cell proteins in order to obtain preparations that are substantially homogeneous as to protein. As a first step, the culture medium or lysate is centrifuged to remove particulate cell debris.

HGF is then purified from contaminant soluble proteins, for example, by an appropriate combination of conventional chromatography methods, e.g. gel filtration, ion-exchange, hydrophobic interaction, affinity, immunoaffinity chromatography, reverse phase HPLC; precipitation, e.g. ethanol precipitation, ammonium sulfate precipitation, or, preferably, immunoprecipitation with anti-HGF (polyclonal or monoclonal) antibodies covalently linked to Sepharose. Due to its high affinity to heparine, HGF can be conveniently purified on a heparin, such as heparine-Sepharose column. One skilled in the art will appreciate that purification methods suitable for native HGF may require modification to account for changes in the character of HGF or its variants upon expression in recombinant cell culture.

As hereinabove described, hHGF contains four putative glycosylation sites, which are located at positions 294 and 402 of the α-chain and at positions 566 and 653 of the β-chain. These positions are conserved in the rat HGF amino acid sequence. Glycosylation variants are within the scope herein.

Glycosylation of polypeptides is typically either N-linked or O-linked. N-linked refers to the attachment of the carbohydrate moiety to the side-chain of an asparagine residue. The tripeptide sequences, asparagine-X-serine and asparagine-X-threonine, wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be involved in O-linked glycosylation. O-linked glycoslation sites may, for example, be modified by the addition of, or substitution by, one or more serine or threonine residue to the amino acid sequence of the HGF molecule. For ease, changes are usually made at the DNA level, essentially using the techniques discussed hereinabove with respect to the amino acid sequence variants.

Chemical or enzymatic coupling of glycosydes to HGF may also be used to modify or increase the number or profile of carbohydrate substituents. These procedures are advantageous in that they do not require production of the polypeptide that is capable of O-linked (or N-linked) glycosylation. Depending on the coupling mode used, the sugar(s) may be attached to (a) arginine and histidine, (b) free carboxyl groups, (c) free hydroxyl groups such as those of cysteine, (d) free sulfhydryl groups such as those of serine, threonine, or hydroxyproline, (e) aromatic residues such as those of phenylalanine, tyrosine, or tryptophan or (f) the amide group of glutamine. These methods are described in WO 87/05330 (published 11 Sep. 1987), and in Aplin and Wriston, *CRC Crit. Rev. Biochem.*, pp. 259–306 (1981).

Carbohydrate moieties present on HGF may also be removed chemically or enzymatically. Chemical deglycosylation requires exposure to trifluoromethanesulfonic acid or an equivalent compound. This treatment results in the cleavage of most or all sugars, except the linking sugar, while leaving the polypeptide intact. Chemical deglycosylation is described by Hakimuddin et al., *Arch. Biochem. Biophys.* 259: 52 (1987) and by Edge et al., *Anal. Biochem.* 118: 131 (1981). Carbohydrate moieties can be removed by a variety of endo- and exoglycosidases as described by Thotakura et al., *Meth. Enzymol.* 138: 350 (1987). Glycosylation is suppressed by tunicamycin as described by Duskin et al., *J. Biol. Chem.* 257: 3105 (1982). Tunicamycin blocks the formation of protein-N-glycosydase linkages.

Glycosylation variants can also be produced by selecting appropriate host cells. Yeast, for example, introduce glycosylation which varies significantly from that of mammalian systems. Similarly, mammalian cells having a different species (e.g. hamster, murine, insect, porcine, bovine or ovine) or tissue (e.g. lung, liver, lymphoid, mesenchymal or epidermal) origin than the source of the HGF variant, are routinely screened for the ability to introduce variant glycosylation.

Covalent modifications of HGF molecule are included within the scope herein. Such modifications are traditionally introduced by reacting targeted amino acid residues of the HGF with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays of HGF or for the preparation of anti-HGF antibodies for immunoaffinity purification of the recombinant glycoprotein. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Derivatization with bifunctional agents is useful for preparing intramolecular aggregates of the HGF as well as for cross-linking the HGF molecule to a water insoluble support matrix or surface for use in assays or affinity purification. In addition, a study of interchain cross-links will provide direct information on conformational structure. Commonly used cross-linking agents include 1,1-bis(diazoacetyl)-2-phenylethane, glutaraldehyde, N-hydroxysuccinimide esters, homobifunctional imidoesters, and bifunctional maleimides. Derivatizing agents such as methyl-3-[(p-azidophenyl)dithio]propioimidate yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,642; 3,969,287; 3,691,016; 4,195,128; 4,247,642; 4,229,537; 4,055,635; and 4,330,440 are employed for protein immobilization and cross-linking.

Certain post-translational modifications are the result of the action of recombinant host cells on the expressed polypeptide. Glutaminyl and aspariginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl or threonyl residues, methylation of the a-amino groups of lysine, arginine, and histidine side chains (T. E. Creighton, *Proteins: Structure and Molecular Properties*, W. H. Freeman & Co., San Francisco, pp. 79–86 (1983)).

Other derivatives comprise those that are covalently bonded to a nonproteinaceous polymer. The nonproteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol.

The HGF may be linked to various nonproteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

The HGF may be entrapped in microcapsules prepared, for example, by coacervation techniques or by interfacial polymerization, in colloidal drug delivery systems (e.g. liposomes, albumin microspheres, microemulsions, nanoparticles and nanocapsules), or in macroemulsions. Such techniques are disclosed in Remington's Pharmaceutical Sciences, 16th Edition, Osol, A., Ed. (1980).

An HGF sequence can be linked to a immunoglobulin constant domain sequence. The resultant molecules are commonly referred to as HGF immunoglobulin chimeras or immunoadhesins. Such chimeras can be constructed essentially as described in WO 91/08298 (published 13 Jun. 1991).

The invention herein also encompasses "molecules with dual specificity for HGF and TGF-β or activin," which would include bispecific antibodies/immunoadhesins and bispecific linear molecules, such as the so-called "Janusin" structures recently reported by Traunecker et al., EMBO, 10: 3655–3659 (1991). Such molecules with dual specificity for HGF and TGF-β or activin would comprise a domain having HGF binding activity and a domain having activin antagonist activity or TGF-β antagonist activity. In one embodiment the molecule is a single-chain polypeptide with an HGF binding activity in one domain and an activin antagonist amino acid sequence or a TGF-β antagonist amino acid sequence in the other domain.

For purposes herein, immunoadhesins are antibody-like molecules which combine the binding specificity of a protein such as a cell-surface receptor, a cell-adhesion molecule or a ligand (an "adhesin"), with the effector functions of immunoglobulin constant domains. Structurally, the immunoadhesins comprise a fusion of an amino acid sequence with the desired binding specificity which is other than the antigen recognition and binding site (antigen combining site) of an antibody (i.e. is "heterologous"), and an immunoglobulin constant domain sequence. The adhesin part of an immunoadhesin molecule typically is a contiguous amino acid sequence comprising at least the binding domain of a receptor (including cell adhesion molecules) or a ligand.

Immunoadhesins can possess many of the valuable chemical and biological properties of human antibodies. Since immunoadhesins can be constructed from a human protein sequence with a desired specificity linked to an appropriate human immunoglobulin hinge and constant domain (Fe) sequence, the binding specificity of interest can be achieved using entirely human components. Such immunoadhesins are minimally immunogenic to the patient, and are safe for chronic or repeated use.

Immunoadhesins reported in the literature include fusions of the T cell receptor* [Gascoigne et al., Proc. Natl. Acad. Sci. USA 84, 2936–2940 (1987)]; CD4* [Capon et al., Nature 337, 525–531 (1989); Traunecker et al., Nature 339, 68–70 (1989); Zettmeissl et al., DNA Cell Biol. USA 9, 347–353 (1990); Byrn et al., Nature 344, 667–670 (1990)]; L-selectin (homing receptor) [Watson et al., J. Cell. Biol. 110, 2221–2229 (1990); Watson et al., Nature 349, 164–167 (1991)]; CD44* [Aruffo et al., Cell 61, 1303–1313 (1990)]; CD28* and B7* [Linsley et al., J. Exp. Med. 173, 721–730 (1991)]; CTLA-4* [Lisley et al., J. Exp. Med. 174, 561–569 (1991)]; CD22* [Stamenkovic et al., Cell 66, 1133–1144 (1991)]; TNF receptor [Ashkenazi et al., Proc. Natl. Acad. Sci. USA 88, 10535–10539 (1991); Lesslauer et al., Eur. J. Immunol. 27, 2883–2886 (1991); Peppel et al., J. Exp. Med. 174, 1483–1489 (1991)]; NP receptors [Bennett et al., J. Biol. Chem. 266, 23060–23067 (1991)]; and IgE receptor α-chain* [Ridgway and Gorman, J. Cell. Biol. 115, abstr. 1448 (1991)], where the asterisk (*) indicates that the receptor is member of the immunoglobulin superfamily.

If the two arms of the antibody-like immunoadhesin structure have two different specificities, the immunoadhesin is referred to as bispecific on the analogy of bispecific antibodies. In the present invention, one arm of the antibody-like, bispecific immunoadhesin structure is comprised of an HGF immunoglobulin chimera with the second arm comprised of an activin or TGF-β antagonist.

As used herein the phrase "bispecific immunoadhesin" designates immunoadhesins (as hereinabove defined) having at least two binding specificities, one of which may be (but does not need to be) an antigen binding site of an antibody. Bispecific immunoadhesins can generally be assembled as hetero-multimers, and particularly as hetero-dimers, -trimers or -tetramers, essentially as disclosed in WO 89/02922 (published 6 Apr. 1989), in EP 314,317 (published 3 May 1989), and in U.S. Pat. No. 5,116,964 issued 2 May 1992.

Bispecific antibodies can, for example, be prepared by the so-called transfectoma method, essentially as described by Morrison, Science, 229: 1202–1207 (1985). This method is also suitable for the production of bispecific immunoadhesins, when a vector comprising the coding sequence of a chimeric (fusion) protein with a desired binding specificity is transfected into a hybridoma secreting an antibody providing the second specificity [see also Berg et al., Proc. Natl. Acad. Sci. USA, 88: 4723 (1991)].

The recombinant production of bispecific immunoadhesins and antibodies is usually based on the co-expression of two immunoglobulin heavy chain-light chain pairs, where the two heavy chains have different specificities. Milstein and Cuello, Nature, 305: 537–539 (1983). Because of the random assortment of immunoglobulin heavy and light chains, these hybridomas (quadromas) produce a potential mixture of 10 different antibody molecules, of which the one having the correct bispecific structure needs to be isolated and purified.

According to an improved method disclosed in co-pending application U.S. Ser. No. 07/931,811 filed 17 Aug. 1992, the disclosure of which is specifically incorporated herein by reference, trimeric bispecific immunoadhesins composed of a hybrid immunoglobulin heavy chain in one arm and a hybrid immunoglobulin heavy chain-light chain pair in the other arm are prepared. These immunoadhesins are preferably produced by individually introducing into suitable host cells the DNA sequences encoding the three immunoglobulin chains making up the trimeric molecule. As a result, the ratios of these DNA sequences can be freely changed. Notwithstanding the absence of the light chain in one arm and the asymmetric structure of the trimeric molecule, these molecules can be efficiently secreted in the form of correctly assembled and folded hetero-trimers. It was further found that the asymmetric structure facilitates the separation of the desired bispecific compound from unwanted immunoglobulin chain combinations, as the presence of an immunoglobulin light chain in only one half of the bispecific molecule provides for a facile way of separation.

In the HGF immunoglobulin chimera, ordinarily, the HGF sequence is fused C-terminally to the N-terminus of the constant region of an immunoglobulin in place of the variable region(s), however N-terminal fusions of the HGF sequence is also desirable. The immunoglobulin constant domain sequence in the HGF immunoglobulin chimeras or immunoadhesins may be obtained from any immunoglobulin, such as IgG-1, IgG-2, IgG-3, or IgG-4 subtypes, IgA, IgE, IgD or IgM.

Typically, such fusions retain at least functionally active hinge, CH2 and CH3 domains of the constant region of an immunoglobulin heavy chain. Fusions are also made to the C-terminus of the Fe portion of a constant domain, or immediately N-terminal to the CH1 of the heavy chain or the corresponding region of the light chain. This ordinarily is accomplished by constructing the appropriate DNA sequence and expressing it in recombinant cell culture. Alternatively, however, the HGF immunoglobulin chimeras or the immunoadhesin may be synthesized according to known methods.

The precise site at which the fusion is made is not critical; particular sites are well known and may be selected in order to optimize the biological activity, secretion or binding characteristics of HGF or the immunoadhesin.

In a preferred embodiment, the C-terminus of a sequence which contains the binding site(s) for an HGF receptor, is fused to the N-terminus of the C-terminal portion of an antibody (in particular the Fe domain), containing the effector functions of an immunoglobulin, e.g. immunoglobulin $G_1$. It is possible to fuse the entire heavy chain constant region to the sequence containing the receptor binding site(s). However, more preferably, a sequence beginning in the hinge region just upstream of the papain cleavage site (which defines IgG Fe chemically; residue 216, taking the first residue of heavy chain constant region to be 114 (Kobet et al., Supra), or analogous sites of other immunoglobulins) is used in the fusion. In a particularly preferred embodiment, the amino acid sequence containing the receptor binding site(s) is fused to the hinge region and CH2 and CH3 or CH1, hinge, $CH_2$ and $CH_3$ domains of an $IgG_1$, $IgG_2$ or $IgG_3$ heavy chain. The precise site at which the fusion is made is not critical, and the optimal site can be determined by routine experimentation.

The bispecific immunoadhesins of the present invention comprise an HGF sequence capable of selective binding to an HGF receptor in one arm, and an activing-antagonist sequence or a TGF-$\beta$ antagonist sequence in the other arm. The activin-antagonist sequence may, for example be a follistatin sequence or a sequence comprising the antibody-antigen combining site of an anti-activin antibody. Similarly, the TGF-$\beta$-antagonist sequence in the other arm. The activin-antagonist sequence may, for example be a follistatin sequence or a sequence comprising the antibody-antigen combining site of an anti-activin antibody. Similarly, the TGF-$\beta$-antagonist sequence may be originated from an anti-TGF-$\beta$ antibody or a TGF-$\beta$-receptor.

For the purpose of the present invention, HGF can be formulated according to known methods to prepare pharmaceutically useful composition, whereby the HGF product is combined in admixture with a pharmaceutically acceptable carrier. Suitable carriers and their formulations are described in *Remington's Pharmaceutical Sciences*, 16th ed., 1980, Mack Publishing Co., edited by Oslo et al., specifically incorporated by reference. These compositions will typically contain an effective amount of the HGF, for example, from on the order of about 0.5 to about 10 mg/ml, together with a suitable amount of carrier to prepare pharmaceutically acceptable compositions suitable for effective administration to the patient. HGF may be administered parenterally or by other methods that ensure its delivery to the bloodstream in an effective form.

Compositions particularly well suited for the clinical administration of HGF include sterile aqueous solutions or sterile hydratable powders such as lyophilized protein. Typically, an appropriate amount of a pharmaceutically acceptable salt is also used in the formulation to render the formulation isotonic.

Dosages and desired drug concentrations of such pharmaceutical compositions may vary depending on the particular use envisioned. A typical effective dose in rat experiments is about 250 µg/kg administered as an intravenous bolus injection. Interspecies scaling of dosages can be performed in a manner known in the art, e.g. as disclosed in Mordenti et al., *Pharmaceut. Res.* 8: 1351 (1991) and in the references cited therein.

Typically, the activin or TGF-$\beta$ antagonist used in the method of this invention is formulated by mixing it at ambient temperature at the appropriate pH, and at the desired degree of purity, with pharmaceutically acceptable carriers, i.e., carriers that are non-toxic to recipients at the dosages and concentrations employed. Suitable carriers and their formulations are described in *Remington's Pharmaceutical Sciences*, 16th ed., 1980, Mack Publishing Co., edited by Oslo et al. These compositions will typically contain an effective amount of the activin antagonist, for example, from on the order of about 0.5 to 10 mg/ml, together with a suitable amount of carrier to prepare pharmaceutically acceptable compositions suitable for effective administration to the patient.

The pH of the formulation depends mainly on the particular type and the concentration of antagonist, but preferably ranges anywhere from about 3 to about 8. Formulation in an acetate buffer at pH 5 is a suitable embodiment.

Compositions particularly well suited for the clinical administration of activin antagonist include sterile aqueous solutions or sterile hydratable powders such as lyophilized protein. Typically, an appropriate amount of a pharmaceutically acceptable salt is also used in the formulation to render the formulation isotonic.

Sterility is readily accomplished by sterile filtration through (0.2 micron) membranes. Activin antagonist ordinarily will be stored as an aqueous solution, although lyophilized formulations for reconstitution are acceptable.

The antagonist composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of activin antagonist to be administered will be governed by such considerations, and is the minimum amount necessary to prevent, ameliorate, or treat the protein-mediated liver disorder. Such amount is preferably below the amount that is toxic to the mammal or renders the mammal significantly more susceptible to infections.

As a general proposition, the pharmaceutically effective amount of the activin or TGF-β antagonist administered parenterally per dose will be in the range of about 0.01 to 100 mg/kg of patient body weight per day, with the typical range of activin antagonist used being about 0.1 to 50 mg/kg/day. Interspecies sealing of dosages can be performed in a manner known in the art, e.g., as disclosed in Mordenti et al., *Pharmaceut. Res.*, 8: 1351 (1991) and in the references cited therein.

HGF and an activin or TGF-β antagonist may be formulated together in a single composition comprising therapeutically effective amounts of each of HGF and antagonist in a pharmaceutically acceptable carrier having appropriate pH for effective administration to the patient. Respective formulations of HGF and the activin of TGF-β antagonist may be combined in vitro before administration or separately administered simultaneously or in tandem, in either order, with any second administration taking place preferably within about 1–24 hours of the first administration and more preferably within about 1–5 hours of the first administration.

The compounds are usually administered as pharmaceutical compositions, usually formulated in dosage forms by methods known in the art; for example, see Remington's Pharmaceutical Sciences, Mack Publishing Company, Easton, Pa., 15th Edition 1975. For parenteral administration, HGF and the activin or TGF-α antagonist are typically formulated in the form of injectable solutions, suspensions or emulsions, in admixture with a suitable pharmaceutically acceptable vehicle and optionally other pharmaceutically acceptable additives. Typical vehicles include saline, dextrose solution, Ringer's solution, etc., but non-aqueous vehicles may also be used.

The term "antidote" as used herein refers to those substances which antagonize the effects of hepatotoxic compounds by inhibiting the binding of a hepatotoxic compound to its receptor, causing a physiological response that opposes the actions of a hepatotoxic compound, changing the chemical nature of a poison to a less toxic form, or decreasing the amount of hepatotoxic compound that reaches its site of action by either preventing its absorption or enhancing its elimination or metabolism. Antidotes are available for only a limited number of hepatotoxic compounds (Smith, C. *Textbook of Pharmacology*, pg. 998 (1992)).

The use of the term "hepatotoxic compound" herein refers to any compound, drug, chemical, or element capable of inducing liver damage upon exposure to the liver.

The term "administration" or "administered" as used herein in reference to HGF refers to that administration of HGF which occurs prior to, simultaneous with, or after administration of or exposure to a hepatotoxic compound, clinical therapy-inducing liver damage, radiation, or other means inducing liver damage. HGF may be combined in vitro with a hepatotoxic compound before administration or separately administered simultaneously or in tandem, in either order, with any second administration taking place generally within about 6 hours of the first administration.

HGF or an activin antagonist may be administered to a subject mammal, preferably human, via any of the accepted modes of administration for agents which exhibit such activity. These methods include subcutaneous and, preferably, parenteral administration. Examples of parental administration routes are intravenous, intrapulmonary, intraarterial, intramuscular, and intraperitoneal administration, the intravenous route being preferred. Administration may be continuous or bolus dosing in sufficient amount to maintain therapeutically effective levels.

HGF may be administered to a subject mammal alone according to the present invention, or combined with other therapies effective in the prevention or treatment of liver damage, such as vascular endothelial growth factor (VEGF) or other growth factors, proteins with growth factor-like activities, such as cytokines or cytokine antagonists or tissue plasminogen activator or other therapeutics.

The use of the term "growth factor" as used herein refers to those factors required to regulate developmental events or required to regulate expression of genes encoding other secreted proteins that may participate in intercellular communication and coordination of development and includes, but is not limited to, insulin-like growth factor-I and II (IGF-I and II), epidermal growth factor (EGF), type a and type b transforming growth factor (TGF-a and TGF-β), epidermal growth factor (EGF), nerve growth factor (NGF), fibroblast growth factor (FGF), platelet-derived growth factor (PDGF), sarcoma growth factor (SGF), granulocytemacrophage colony stimulating growth factor (GM-CSF), vascular endothelial growth factor (VEGF), and hemopoietic growth factors.

VEGF is a specific mitogen for endothelial cells that acts to increase microvascular permeability. VEGF is expressed in many normal adult organs, including, lung, kidney, adrenal gland, heart, liver, and stomach mucosa, as well as in elicited peritoneal macrophages. Berse et al., Supra demonstrate particularly high VEGF mRNA levels in several human tumors, where it may be involved in promoting tumor angiogenesis and stroma generation, both as an endothelial cell mitogen and indirectly by its permeability enhancing effect that leads to the deposition of a provisional fibrin gel matrix. The mRNA sequence of VEGF is described in Leung et al., (*Science* 246: 1306–1309 (1989)).

Tissue plasminogen activator (tPA) is an enzyme that has the potent ability to dissolve blood clots in vivo and is used as a therapeutic in the treatment of vascular diseases, such as myocardial infarction. A substantially pure form of tPA was first produced from a natural source and tested for in vivo activity by Collen et al., U.S. Pat. No. 4,752,603. Pennica et al., (*Nature* 301: 214 (1983)) determined the DNA sequence of tPA and deduced the amino acid sequence from this DNA sequence (see U.S. Pat. No. 4,766,075, issued 23 Aug. 1988). TPA has been shown to be useful in the treatment of veno occlusive disease (VOD) (Baglin et al., *Bone Marrow Transplant* 5(6): 439–441 (1990)) and (Rosti et al., *Lancet* 339: 1481–1482 (1992)).

Cytokines are secreted peptides or proteins that regulate the intermediary metabolism of amino acids, proteins, carbohydrates, lipids and minerals. Cytokines include peptides or proteins that act to mediate inflammation and are involved in intercellular communication modulating cell proliferation, and adhesion of inflammatory cells to the walls of the vessels, and to the extra cellular matrix. Cytokines are essential for the communication between the liver and extrahepatic sites and within the liver itself. Cytokines interact with hormones such as glucocordicoids, resulting in a complex network of mutual control. Many cytokines exert growth factor-like activity in addition to their specific proinflammatory effects. The liver is an important site of cytokine synthesis and the major clearance organ for several cytokines. In liver disease, cytokines are involved in the onset of intrahepatic immune responses, in liver regeneration, and in the fibrotic and cirrhotic transformation of the liver (Andus et al., *Hepatology* 13(2): 364–375 (1991)). Cytokines include, but are not limited to, the interleukin family of peptides and proteins; interferons-alpha,-beta,gamma; tumor necrosis factors-alpha and -beta; and prostaglandins E1 and E2.

The use of the term "therapeutic" as used herein refers to those agents effective in the prevention or treatment of a disorder or pathologic physiological condition.

Further details of the invention are illustrated in the following non-limiting example.

EXAMPLE 1

A. Recombinant Production of hHGF

Recombinant hHGF (rhHGF) was produced as described in copending U.S. application Ser. No. 07/712,284, filed 10 Jun. 1991.

An hHGF cDNA clone (HLC3) isolated from a human leukocyte library as described by Seki et al., Supra, was cloned into the broadly applicable parental expression vector pSVI6B5. pSVI6B5 carries polylinker regions which provide convenient, unique restriction endonuclease recognition sites that can be used to introduce any sequence that encodes a polypeptide of interest.

CHO-dhfr$^-$ cells (Urlaub et al., Proc. Natl. cad. Sci. USA 77: 4216–4220 (1980)) were contransfected with the above-described pSVI6B5-based hHGF expression vector and with a dhfr selection vector pFD11 (Simonsen and Levinson, Proc. Natl. Acad. Sci. USA 80: 2495–2499 (1983) using the general procedure of Graham and van des Eb, Virology 52: 456–467 (1973)). The latter plasmid encodes DHFR, thereby conferring methotrexate resistance on the transfected cells and allowing for selection of hHGF expressing transformants. The transformed dhfr$^-$ cells were selected by growth in glycine-, hypoxanthine- and thymidine-deficient medium. Colonies that arose on this selection medium were isolated using cotton swabs and propagated in the same medium to several generations. After cell growth, the cells were amplified and selected with increasing amounts of methotrexate using standard techniques. Clones that could grow in selective media, and therefore incorporated the transfected DHFR containing plasmid, were screened for the presence of secreted HGF. HGF activity in the media of these clones was assayed with the mitogenic assay described hereinbelow. Alternatively, HGF activity in culture media may also be measured by incorporation of $^{125}$I-labelled deoxyuridine into rat hepatocyte in primary culture as described by Nakamura et al., Nature 342, 440–443 (1989). hHGF was purified essentially as described by Nakamura et al., Supra.

B. Protection from Hepatotoxicity by Treatment with rhHGF

We have examined the effects of HGF in combination therapy with BiCNU®-Carmustine (Bristol-Myers Squibb Company, Oncology division), in male F344 rats, body weighing 190–260 grams each.

Carmustine chemically is 1,3-bis (2-chloroethyl)-1-nitrosourea and belongs to a group of chemotherapeutics used in the treatment of certain neoplastic diseases. BiCNU® is used in brain tumors, both primary and metastatic; multiple myeloma; Hodgkin's disease, as a secondary therapy; and non-Hodgkin's lymphoma, as a secondary therapy.

One adverse reaction to BiCNU® is hepatotoxicity manifested by increased transaminase, alkaline phosphatase and bilirubin levels Patients receiving high dose treatment (usually with bone marrow transplantation) are in danger of developing hepatic veno-occlusive disease (VOD) which will present with hepatomegaly (enlargement of the liver) and ascites (accumulation of fluid). These findings are clinically similar to Budd-Chiari syndrome. About 20% of bone marrow transplantation patients develop this syndrome and in about 47% of these patients the severe form of VOD is fatal. Other adverse reactions include delayed cumulative myclosuppression, thrombocytopenia more severe than leucopenia and anemia, dose dependent pulmonary toxicity characterized by pulmonary fibrosis with delayed onset (even years), and nephrotoxicity, with progressive azotemia and decrease in kidney size and renal failure.

BiCNU® is supplied as lyophilized yellow flakes with a molecular weight of 214.06. It is soluble in lipids and alcohol. For human use, after reconstitution of 100 mg of BiCNU® in 3 mls of ethanol, 27 mls of sterile water is added for injection purposes and the drug is administered intravenously.

Protocol:

The concentration of rhHGF used was 2.45 mg/ml, and the dose was 280 ug/kg of body weight delivered in 0.25 ml of Vehicle (phosphate buffered saline (PBS)+0.1% bovine serum albumin (BSA), sterilized) injected intravenously (IV) at −30 min., 6, 12, 24, 30, and 36 hours.

In the rat, the dose of BiCNU®-was 50 mg/kg of body weight administered in a single intraperitoneal (IP) injection at 0 hours. The vehicle was peanut oil and the whole dose was delivered in 1.5 ml. Using the toxicokinetic sealing method of Mordenti et al., ("The Use of Interspecies Sealing in Toxicokinetics", Toxicokinetics and New Drug Development, A. Yacobi et al., eds. Pergamon Press, New York p42–96 [1989]) and Chappel et al. ("Extrapolation of Toxicological and Pharmacological Data from Animals to Humans", Advances in Drug Research, Vol 20 B. Testa, Ed., Academic Press, San Diego, pp 1–116 [1991]) the 50 mg/kg dose in rats equals a 9.2 mg/kg dose in humans. Clinical dose of BiCNU® used in humans is 5–15 mg/kg.

Samples were collected at 48 hours after IP injection of BiCNU®. One set of 7 rats received a combination of rhHGF with BiCNU®, and one set of 7 rats received BiCNU® plus the rhHGF vehicle. One set of 7 animals received I.P. peanut oil plus the rhHGF vehicle and served as controls.

Figure 1B:
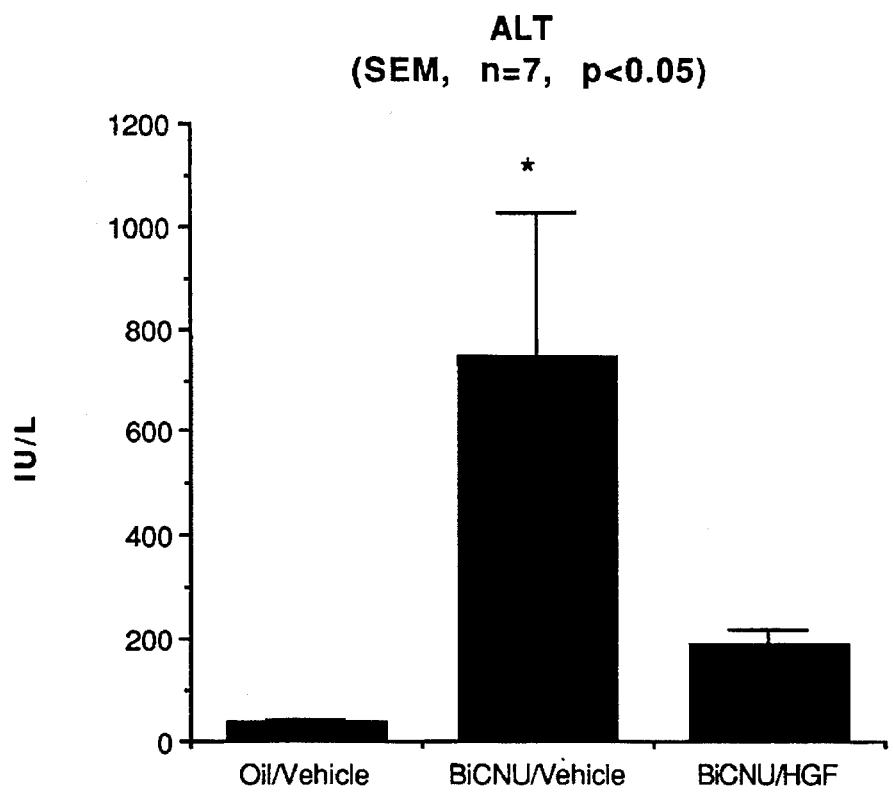
Figure 1C:
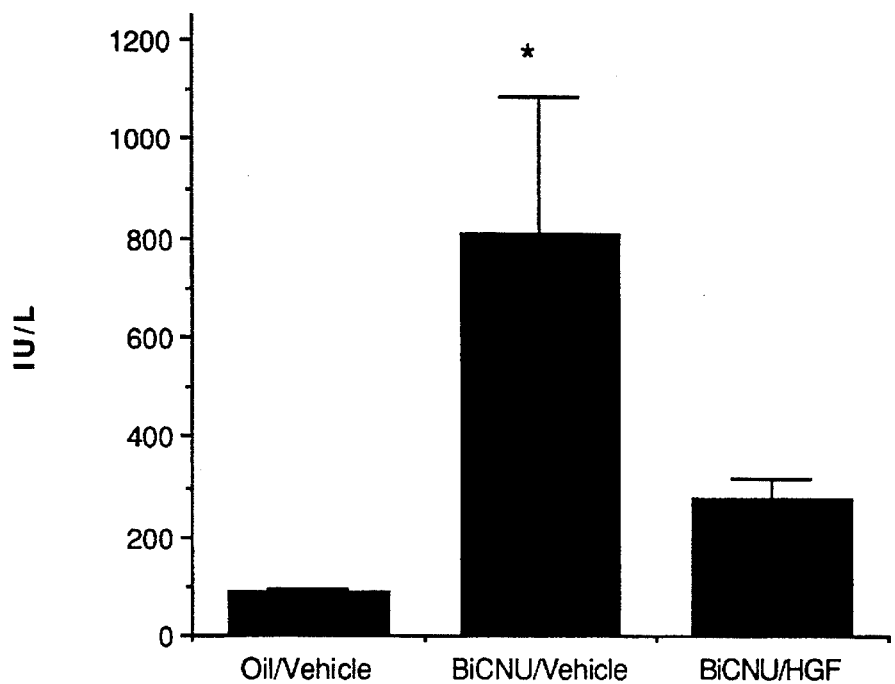
Figure 1D:
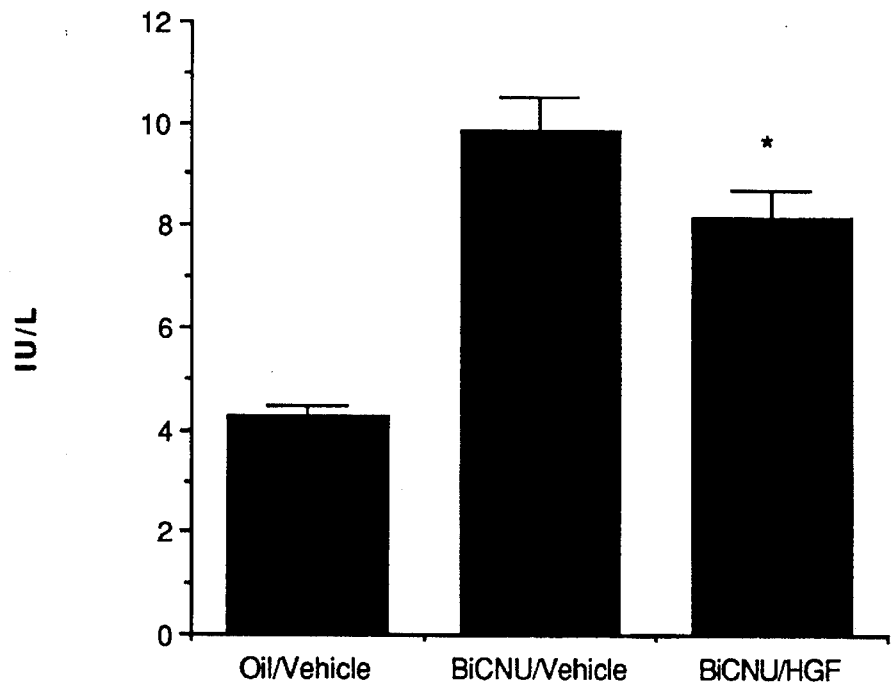
Figure 1E:
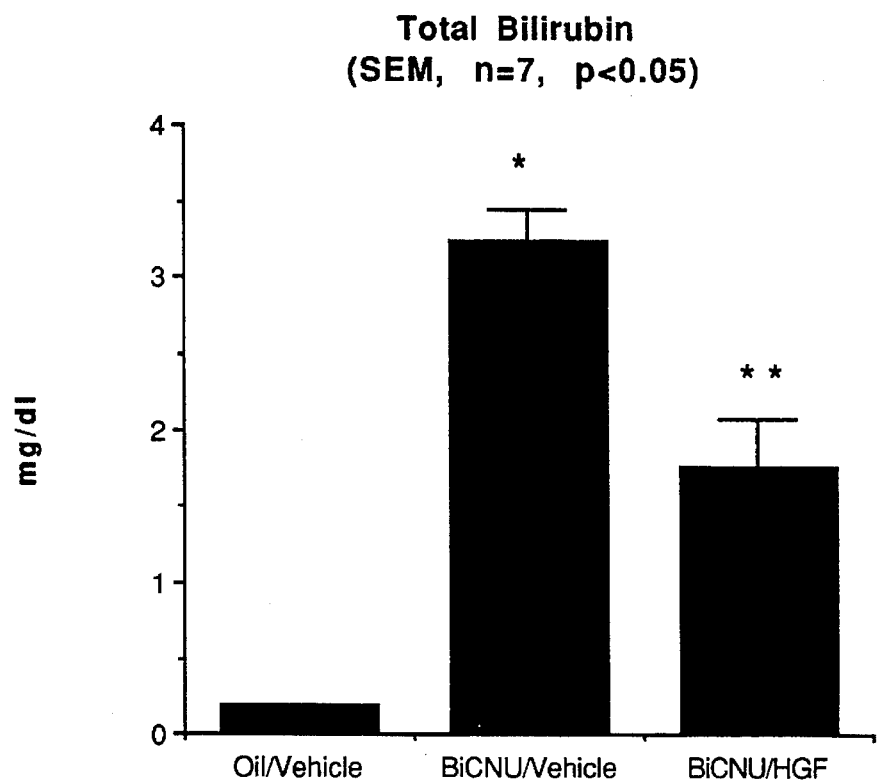
Figure 1F:
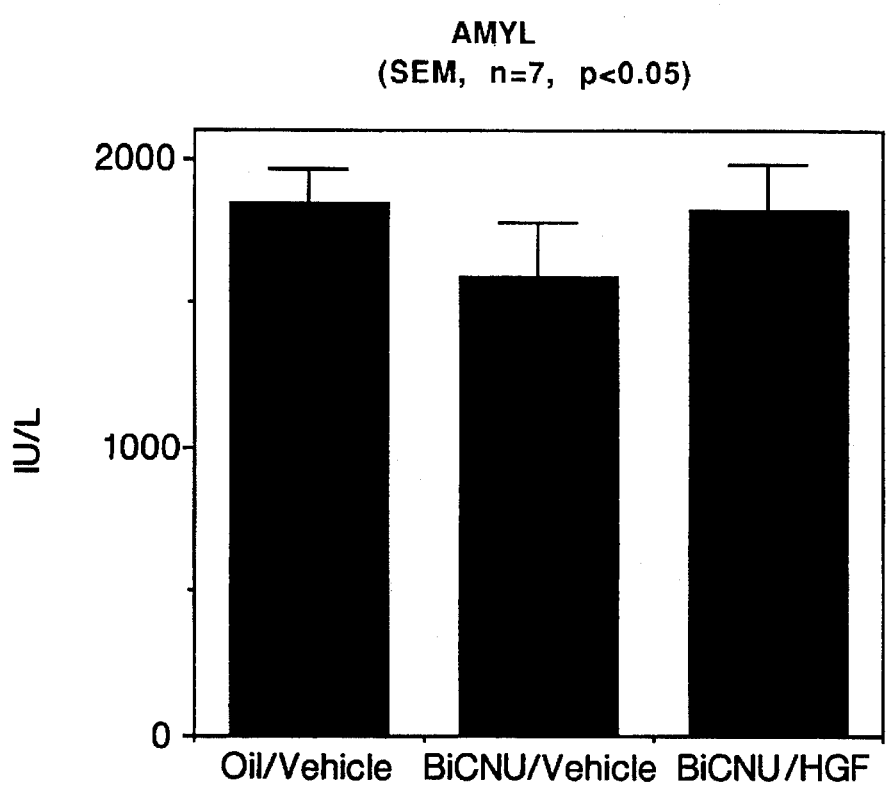

Results:

As shown in FIGS. 1(a)–1(e), animals receiving combination therapy of BiCNU® and rhHGF showed decreased levels of alkaline phosphatase (FIG. 1(a)), alanine aminotransferase (FIG. 1(b)), aspartate aminotranferase (FIG. 1(c)), g-glutamyl transpeptidase (FIG. 1(d)), and total bilirubin (FIG. 1(e)) from those animals receiving BiCNU® alone.

Protocol for the liver histopathology study:

One set of 7 animals received I.P. peanut oil only and served as controls. Fourteen other rats were inoculated with BiCNU® in peanut oil at 50 mg/kg body weight, and 7 of the 14 rats received rhHGF (280 µg/kg body weight I.V. at −30 minutes, 6, 12, 24, 30, and 36 hours. All rats were euthanasia by $CO_2$ at 48 hours after inoculation of BiCNU® or oil I.P. Sections of liver, sternum, lung, kidney, and spleen were fixed in formalin, sectioned in paraffin, stained with H & E, and examined histologically.

Figure 2A:
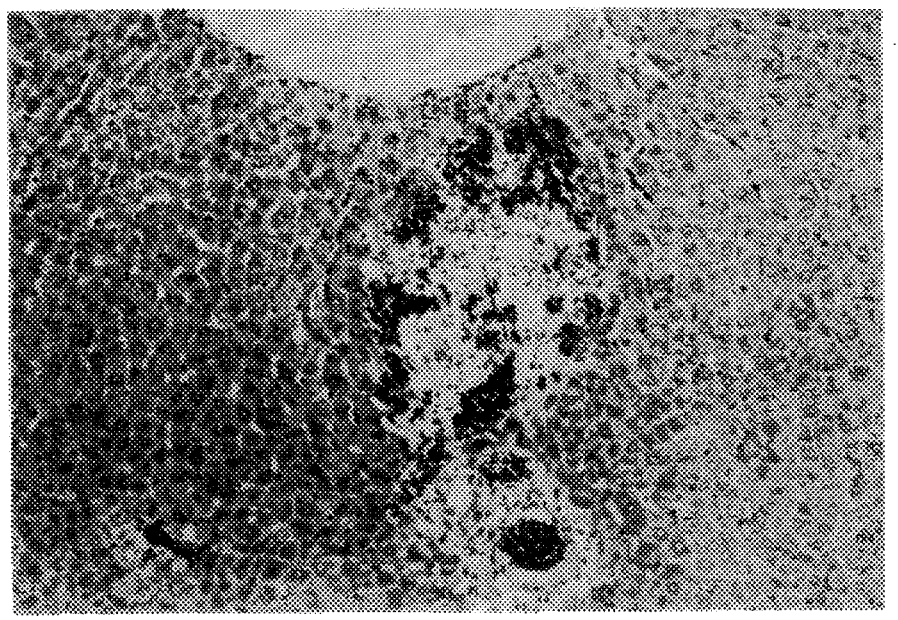
FIG. 2(A) shows hepatocellular necrosis with accompanying hemorrhage which extends from the portal triad almost to the central vein in a rat treated with BiCNU®.
Figure 2B:
FIG. 2 (B) shows the lack of hepatocellular necrosis in the liver of an rhHGF-treated, BiCNU exposed rat. The treatments were performed as described in the Example.

Histopathology Results:

Lesions were consistently present in the liver, bone marrow, and spleen of rats which received BiCNU®. BiCNU® induces biliary necrosis and hepatocellular necrosis in rats. Rats which receive rhHGF have biliary necrosis comparable to that in untreated rats and rhHGF reduces the severity of hepatocellular necrosis seen in rats treated with BiCNU® alone, as shown in FIGS. 2(a) and 2(b).

EXAMPLE 2

This example shows HGF protection against Activin and TGF-b induced Hepatocyte death.

Method

Hepatocytes were obtained from adult female Sprague-Dawley rats by collagenase perfusion, as described by Garrison and Haynes. The cells were plated at a density of 4000 cell/well in 96-well microtiter plates (Falcon). The culture medium was William's E medium supplemented with penicillin (100 U/ml), streptomycin sulfate (100 µg/ml), L0glutamine (2 mM), transferrin (10 µg/ml), and trace elements (0.01%). The cells were plated in medium containing 5% fetal bovine serum at 37° C. in 5% $CO_2$. After 16 hours, the plating medium was replaced with 100 µl serum-free medium containing: no additions for the control; HGF at 10, 100, 1000 ng/ml; activin-A (10 ng/ml) alone or in combination with HGF at 10, 100, 1000 ng/ml; or TGF-b (1 ng/ml) alone or in combination with HGF at 10, 100, 1000 ng/ml.

Twenty four hours later, viability was assessed by measuring the reduction of MTT, an index of mitochondrial function, essentially as described by Carmichael et al. (*Cancer Res* 47: 936–942 [1987]). MTT was dissolved to 5 mg/ml in phosphate-buffered saline and 5 µl was immediately added to each well. After incubation at 37° C. for 4 hours, the media was removed by gently inverting the plate and blotting on a paper towel. The cells were solubilized by addition of 100 µl DMSO followed by shaking for 5 minutes on an orbital shaker. The absorbance at 560 nm, less the absorbance at the reference wavelength of 690 nm, was measured in an automatic plate reader (SLT Lab Instruments). In some experiments in which cells were cultured in more than one microtiter plate, data were normalized to the controls in each plate.

Results

Figure 3:
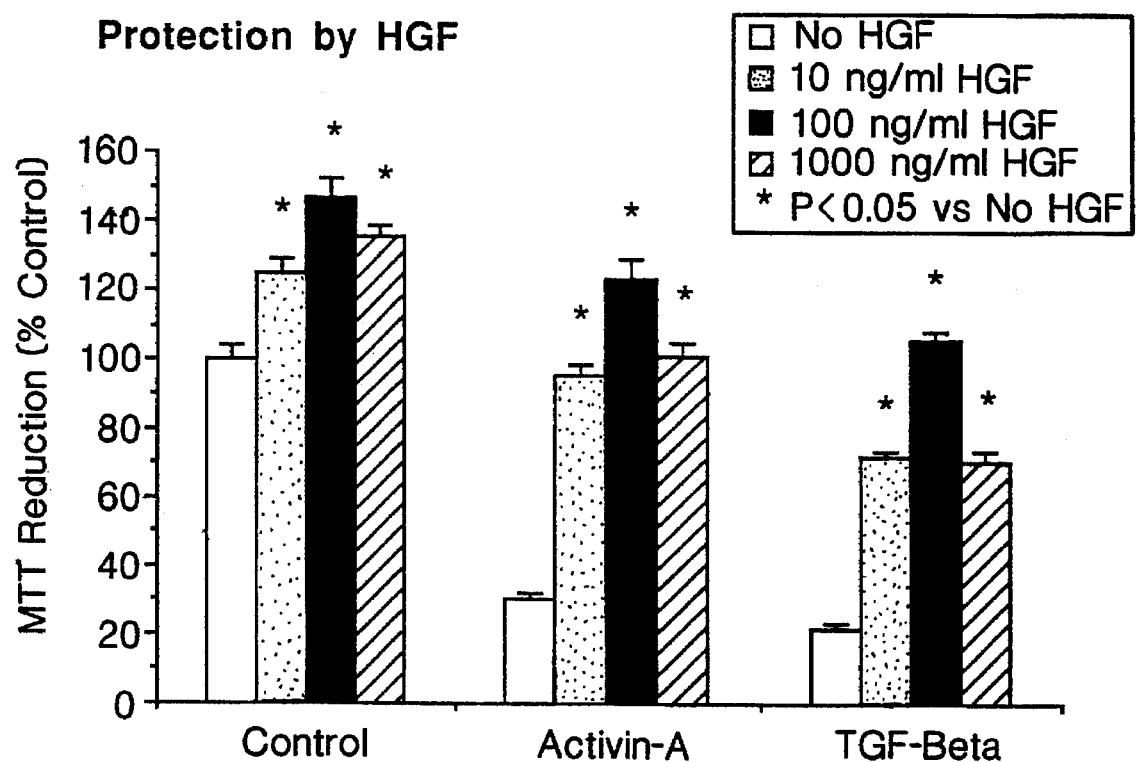
FIG. 3 shows HGF protection against liver damage induced by Activin-A or TGF-β as measured by MTT reduction by the method of Carmichael et al. (*Cancer Res* 47: 936–942 [1987]).

As shown in the FIG. 3, HGF causes a small increase in viability in control cultures, as measured by MTT reduction, which is an index of mitochondrial function. Activin caused viability to be reduced by about 70%, but this effect was substantially abrogated if the culture medium also contained HGF. Similarly, TGF-b caused a large decrease in hepatocyte viability, and as with activin, this effect was largely prevented by inclusion of HGF.

EXAMPLE 3

This example shows the use of HGF co-administered with an activin antagonist to provide protection from liver damage.

Methods

A transgenic mouse expressing hepatitis B virus proteins is used to determine the preventative effect provided by co-administration of HGF with follistatin. Suitable transgenic mice are the two generically different categories of HBV-transgenic mice (lineages 23-3 and 80-219) described and used in Gilles et al., (*J Virol.*, 66: 3955–3960 (1992)).

Recombinant HGF is produced as described in Example 1. The concentration of rhHGF used is 2.45 mg/ml and the dose is 280 µg/kg of body weight delivered in 0.25 ml of Vehicle (phosphate buffered saline (PBS)+0.1% bovine serum albumin (BSA, sterilized) and injected intravenously (IV). The dose of follistatin used is in the range of about 0.1 to 100 mg/kg of patient body weight per day and is delivered by intravenous injection (IV). Interspecies scaling of dosages can be performed in a manner known in the art, e.g., as disclosed in Mordenti et al Supra and in the references cited therein.

One set of animals receives vehicle only and serves as a control. Another set of animals is injected with rhHGF every 6 hours over a 10 day period. A third set of animals is injected with rhHGF and follistatin in combination every 6 hours over a 5 day period. After 1, 3, and 5, days of injections, the mice were anesthetized with ketamine-xylazine, and blood was collected by cardiac puncture and allowed to clot for one hour at room temperature. Serum aliquots are stored at –70° C. prior to measurement of bilirubin, ALT, and AST on a Monarch Model 7000 automated analyzer. The liver is dissected free from connective tissue and weighed, and pieces are fixed in neutral buffer formalin. Paraffin-embedded sections are cut at 4 µm stained with hematoxylin and cosin and examined histologically.

It is reasonably expected that the transgenic mouse data resulting from Example 3 may be extrapolated to horses, cows, and other mammals, correcting for the body weight of the mammal in accordance with recognized veterinary and clinical procedures. Using standard protocols and procedures, the veterinarian or clinician will be able to adjust the doses, scheduling, and mode of administration of the HGF and activin antagonist to achieve maximal effects in the desired mammal being treated. Humans are believed to respond in this manner as well.

Although the foregoing refers to particular preferred embodiments, it will be understood that the present invention is not so limited. It will occur to those ordinarily skilled in the art that various modifications may be made to the disclosed embodiments without diverting from the overall concept of the invention. All such modifications are intended to be within the scope of the present invention.

All citations cited throughout the specification and the references cited therein, are hereby expressly incorporated by reference.

We claim:

1. A molecule comprising:
    a first domain comprising HGF; and
    a second domain comprising an activin antagonist or a TGF-β antagonist.

2. The molecule of claim 1, wherein said molecule is a single-chain polypeptide with an HGF amino acid sequence in the first domain, and an activin antagonist amino acid sequence or a TGF-β antagonist amino acid sequence in the second domain.

3. The molecule of claim 2, further comprising an immunoglobulin sequence.

4. The molecule of claim 1, wherein the second domain comprises an anti-activin antibody or an anti-TGF-β antibody.

5. The molecule of claim 1, wherein said HGF is fused to an immunoglobulin sequence.

6. The molecule of claim 1, wherein said molecule is a bispecific immunoadhesin comprising:
    an HGF amino acid sequence fused to an immunoglobulin sequence; and an activin antagonist or a TGF-β antagonist.

7. The molecule of claim 6, wherein said activin antagonist or TGF-β antagonist comprises an antigen binding site of an immunoglobulin sequence.

8. The molecule of claim 6, wherein said bispecific immunoadhesin includes a first arm comprising an HGF amino acid sequence and a second arm comprising an activin antagonist amino acid sequence or a TGF-β antagonist amino acid sequence.

9. The molecule of claim 8, wherein said activin antagonist comprises follistatin.

10. The molecule of claim 8, wherein said activin antagonist is an antigen-antibody combining site of an anti-activin antibody.

11. The molecule of claim 6, wherein said bispecific immunoadhesin comprises an HGF amino acid sequence and a TGF-β antagonist amino acid sequence fused to an immunoglobulin sequence or an HGF amino acid sequence and an activin antagonist sequence fused to an immunoglobulin sequence.

12. A molecule comprising:
    a first domain comprising HGF; and
    a second domain comprising an activin antagonist.

13. The molecule of claim 12, wherein said activin antagonist comprises follistatin.

14. A molecule comprising:
    a first domain comprising HGF; and
    a second domain comprising a TGF-β antagonist.

15. The molecule of claim 14, wherein said TGF-β antagonist comprises a soluble form of a TGF-β receptor.

16. A bispecific immunoadhesin comprising HGF fused to an immunoglobulin sequence, wherein the immunoglobulin sequence comprises an anti-activin or anti-TGF-β antibody.

17. A bispecific immunoadhesin comprising HGF and follistatin, each fused to an immunoglobulin sequence.

18. The molecule of claim 1, wherein said HGF is hHGF.

* * * * *

UNITED STATES PATENT AND TRADEMARK OFFICE
CERTIFICATE OF CORRECTION

PATENT NO. : 5,654,404

DATED : August 5, 1997

INVENTOR(S) : Roos et al.

It is certified that error appears in the above-identified patent and that said Letters Patent is hereby corrected as shown below:

In column 5, line 30: insert --glucose production by hepatocytes (Mine et al.,*Endocrinology*. 125: 586-591 [1989]), induction of-- after the word "of".

In column 12, line 21: insert --is used to designate an amount effective in achieving prevention as hereinabove defined.
Patients "at risk of developing liver damage"-- after the word "amount".

In column 14, line 42: before --Xaa-- first occurrence insert inside margin.

In column 27, line 46: "$CH_2$ and $CH_3$" should read --CH2 and CH3--.

In column 27, line 52: "activing-" should read --activin- --.

In column 27 lines 56 to 60: delete "Similarly, the TGF-B-antagonist sequence in the other arm. The activin-antagonist sequence may, for example be a follistatin sequence or a sequence comprising the antibody=antigen combing site of an anti-activin antibody.".

UNITED STATES PATENT AND TRADEMARK OFFICE
CERTIFICATE OF CORRECTION

PATENT NO. :   5,654,404

DATED       :   August 5, 1997

INVENTOR(S) :   Roos et al.

It is certified that error appears in the above-identified patent and that said Letters Patent is hereby corrected as shown below:

In column 29, line 14:  "of" should read --or--.

In column 29, line 25:  "TGF-a" should read --TGF-B--.

Signed and Sealed this

Fifth Day of May, 1998

Attest:

BRUCE LEHMAN

Attesting Officer                Commissioner of Patents and Trademarks